United States Patent [19]

Hung et al.

[11] Patent Number: 4,788,285

[45] Date of Patent: Nov. 29, 1988

[54] INDOLE-PHTHALIDE DERIVATIVES

[76] Inventors: William M. Hung, 91760 Millcliff Dr., Cincinnati, Ohio 45231; Angelique M. Black, 115 Meadow Hill Dr., Covington, Ky. 41017

[21] Appl. No.: 129,620

[22] Filed: Dec. 7, 1987

Related U.S. Application Data

[62] Division of Ser. No. 937,782, Dec. 4, 1986, Pat. No. 4,736,027, which is a division of Ser. No. 745,555, Jun. 17, 1985, Pat. No. 4,660,060.

[51] Int. Cl.$^4$ .................. C07D 405/04; C07D 405/14; C07D 413/14
[52] U.S. Cl. .................. 544/144; 546/201; 548/463
[58] Field of Search .................. 544/144; 546/201; 548/463

[56] References Cited

U.S. PATENT DOCUMENTS

| | | | |
|---|---|---|---|
| 3,491,116 | 1/1970 | Lin | 548/463 |
| 4,062,866 | 12/1977 | Garner et al. | 548/463 |

FOREIGN PATENT DOCUMENTS 1422096  1/1976  United Kingdom .

*Primary Examiner*—Robert W. Ramsuer
*Attorney, Agent, or Firm*—Terrence E. Miesle

[57] ABSTRACT

3-(1-R-2-$R^1$-5/6-Y-indol-3-yl)-3-(2-$R^2$-4-N-$R^3$-N-$R^4$-aminophenyl)-X-phthalides, 7-(1-R-2-$R^1$-5/6-Y-indol-3-yl)-7-(2-$R^2$-4-N-$R^3$-N-$R^4$-aminophenyl)furo[3,4b]-pyridine-5(7H)-ones and 5-(1-R-2-$R^1$-5/6-Y-indol-3-yl)-5-(2-$R^2$-4-N-$R^3$-N-$R^4$-aminophenyl)furo[3,4b]-pyridine-7(5H)-ones are useful as color formers in transfer imaging systems, pressure-sensitive carbonless duplicating systems and thermal-responsive marking systems. The phthalides are prepared by the interaction of the corresponding 2-(1-R-2-$R^1$-5/6-Y-indol-3-yl)carbonyl-X-benzoic acid with the corresponding 3-$R^2$-N-$R^3$-N-$R^4$-aniline or the interaction of the corresponding 2-(2-$R^2$-4-N-$R^3$-N-$R^4$-aminophenyl)carbonyl-X-benzoic acid with the corresponding 1-R-2-$R^1$-5/6-Y-indole. The furopyridines are prepared by the interaction of the corresponding 2/3-(1-R-2-$R^1$-5/6-Y-indol-3-yl)carbonylpyridine-3/2-carboxylic acid with the corresponding 3-$R^2$-N-$R^3$-N-$R^4$-aniline. The novel 1-R-2-$R^1$-5/6-Y-indol-3-yl)carbonyl-X-benzoic acids and 1-R-2-$R^1$-5/6-Y-indoles are useful as intermediates to the appropriate phthalides and furopyridinones.

1 Claim, No Drawings

INDOLE-PHTHALIDE DERIVATIVES

This application is a division of application Ser. No. 937,782, filed Dec. 4, 1986, now U.S. Pat. No. 4,736,027, which is in turn a division of application Ser. No. 745,555, filed June 17, 1985, now U.S. Pat. No. 4,660,060.

BACKGROUND OF THE INVENTION (a) Field of the Invention

The invention described herein relates to novel compounds classified in the field of organic chemistry as phthalides, useful as color-forming substances, particularly in the art of transfer imaging and pressure-sensitive and thermal responsive carbonless duplicating; to transfer imaging systems containing said compounds; to pressure-sensitive and thermal responsive carbonless duplicating systems containing said compounds; to novel 2-indolylcarbonylbenzoic acids, useful as intermediates to said phthalides; to novel indoles, useful as intermediates to said phthalides and to said benzoic acids; and to processes for preparing said phthalides, benzoic acids and indoles.

(b) Information Disclosure Statement

Several classes of organic compounds of widely diverse structural types are known to be useful as colorless precursors for transfer imaging systems. Among the more important classes, there may be named leuco-type dyestuffs such as: phthalides, for example, crystal violet lactone, Malachite green lactone; fluoran, for example, 3-dialkylamino-7-dialkylaminofluoran, 3-dimethylamino-6-methoxyfluoran; phenothiazines, for example, benzoyl leuco methylene blue; Rhodamines, for example, Rhodamine-B-anilinolactone; and spirodinaphthopyrans, for example, 3-methyl-spiro-dinaphthopyran. The classes of organic compounds listed above also generally find utility in pressure-sensitive and thermal responsive carbonless duplicating systems.

Typical of the transfer imaging systems is the system described in U.S. Pat. No. 4,399,209 which issued Aug. 16, 1983. In this patent a transfer imaging system is disclosed wherein images are formed by image-wise exposing a layer comprising a chromogenic material and pressure rupturable containing as an internal phase, a photosensitive composition. In this system the chromogenic material is encapsulated with the photosensitive compound. Upon exposure to filtered U.V. or blue light in the wavelength range of 380 to 480 nanometer a certain portion of the capsules will harden. The capsules in which the internal phase has remained liquid are ruptured and the chromogenic material is image-wise transferred to a developer or copy sheet where the chromogenic material reacts with a developer to form an image.

Typical of the many commercially accepted pressure-sensitive and thermal-responsive carbonless copy systems are those described in U.S. Pat. Nos. 2,712,507; 2,800,457; 3,041,289; and 4,000,087, which issued July 5, 1955; July 23, 1957; June 26, 1962; and Dec. 28, 1976, respectively.

Many of the color formers in the prior art suffer one or more disadvantages such as low tinctorial strength, low resistance to sublimation, low susceptibility to copiability of the color-developed images in standard office copying machines, for example, a xerographic type of copier, poor image stability in the pressence of light, i.e., the product image fades losing intensity or changes to a less acceptable color, and low solubility in common organic solvents. The latter disadvantage requires the use of specialized and expensive solvents in order to obtain microencapsulated solutions of sufficient concentration for use in pressure-sensitive copying systems and transfer imaging systems.

The following items to date appear to constitute the most relevant prior art with regard to the instant invention.

U.S. Pat. No. 4,062,866, issued Dec. 13, 1977 discloses phthalides having the structural formula.

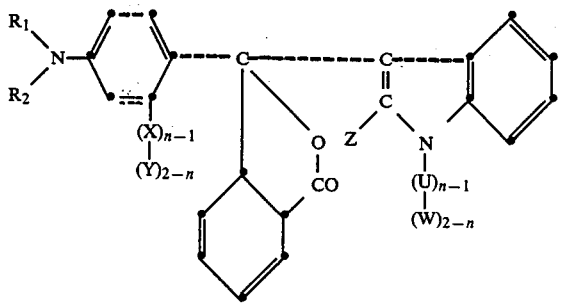

wherein $R_1$ and $R_2$ independently of the other, represent hydrogen, alkyl with 1 to 12 carbon atoms, alkoxyalkyl with 2–8 carbon atoms, cycloalkyl with 5 or 6 carbon atoms, benzyl or phenyl, X represents alkyl with 1 to 12 carbon atoms, alkoxy with 1 to 12 carbon atoms or acyloxy with 2 to 12 carbon atoms, Y represents alkyl with 2 to 12 carbon atoms, alkoxy with 3 to 12 carbon atoms or acyloxy with 2 to 12 carbon atoms, Z represents hydrogen, alkyl having 1 to 12 carbon atoms or phenyl, U represents alkyl having 3 to 12 carbon atoms, benzyl or cyanoethyl, or may also represent W when $R_1$ and $R_2$ both are benzyl, W represents hydrogen, methyl or ethyl and n is 1 or 2, the benzene rings A and B may be substituted by alkyl with 1 to 6 carbon atoms and the benzene ring B may also be substituted by nitro or halogen. The phthalides are particularly useful as color formers which give intense blue colors when they are contacted with an electron-accepting co-reactant such as silton clay or a phenolic resin.

British Patent No. 1,422,096, which was published Jan. 21, 1976 discloses phthalides having the structural formula

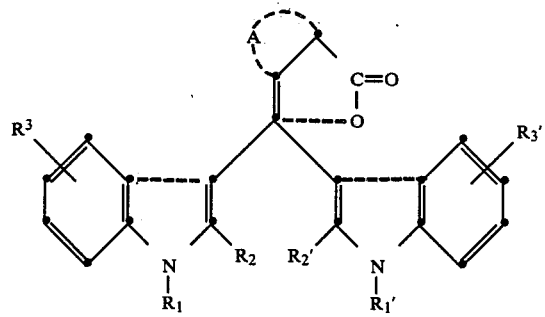

wherein A together with the carbon atoms to which it is attached represents an unsubstituted benzene ring; a naphthalene or a heterocyclic ring; $R_2$ and $R_2$ each independently represents hydrogen, $C_{1-4}$ alkyl or aryl; $R_3$ and $R_3$ independently represent hydrogen, $C_{1-4}$ alkyl or $C_{1-4}$ alkoxy; and $R_1$ and $R_1$ each independently represents hydrogen, aralkyl, unsubstituted or substituted (excluding aryl substituents) $C_{1-18}$ alkyl or unsubstituted or substituted $C_{3-18}$ alkenyl. The phthalides are particularly useful as color formers in heat-sensitive recording material.

U.S. Pat. No. 3,491,116, issued Jan. 20, 1970, discloses phthalides having the structural formula

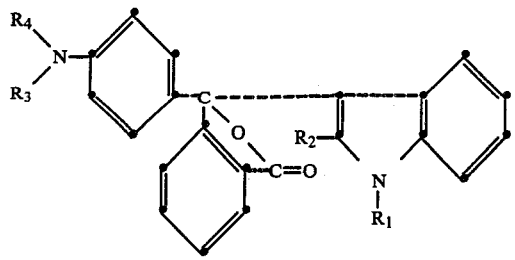

wherein $R_1$ and $R_2$ comprise alkyl radicals having from one to five carbon atoms, aryl radicals, and hydrogen; and $R_3$ and $R_4$ comprise alkyl radicals having from one to five carbon atoms and hydrogen. The phthalides are particularly useful as color formers in pressure-sensitive recording material which contain Lewis acid molecules as color developers.

U.S. Pat. No. 4,399,209, issued Aug. 16, 1983, discloses a transfer imaging system in which images are formed by image-wise reaction of one or more chromogenic materials and a developer, said system comprising: an imaging sheet comprising a first substrate; a chromogenic material; a radiation curable composition which undergoes an increase in viscosity upon exposure to actinic radiation; a coating on one surface of said first substrate comprising said chromogenic material and said radiation curable composition; said radiation curable composition being encapsulated in rupturable capsules as an internal phase; and a developer sheet comprising a second substrate and a developer material capable of reacting with said chromogenic material to form an image on one surface of said second substrate; wherein images are formed by image-wise exposing said coating to actinic radiation, and rupturing capsules in the image areas with said coating in facial contact with said developer sheet such that said internal phase is image-wise released from said ruptured capsules and there is imagewise transfer of said chromogenic material to said developer sheet and a patterned image-forming reaction occurs between said chromogenic material and said developer material.

SUMMARY OF THE INVENTION

In the first of its composition of matter aspects, the invention relates to certain 3-(1-R-2-$R^1$-5/6-Y-indol-3-yl)-3-(2-$R^2$-4-N-$R^3$-N-$R^4$-aminophenyl)-X-phthalides useful in transfer imagng systems and pressure-sensitive and thermalresponsive carbonless duplicating systems.

In the second of its composition of matter aspects, the invention relates to a compound selected from the group consisting of 7-(1-R-2-$R^1$-5/6-Y-indol-3-yl)-7-(2-$R^2$-4-N-$R^3$-N-$R^4$-aminophenyl)furo [3,4b]-pyridine-5(7H)-ones and 5-(1-R-2-$R^1$-5/6-Y-indol-3-yl)-5-(2-$R^2$-4-N-$R^3$-N-$R^4$-aminophenyl)furo [3,4b]-pyridine-7(5H)-ones and mixtures thereof useful in transfer imaging system and pressure-sensitive and thermal-responsive carbonless duplicating systems.

In the third of its composition of matter aspects, the invention relates to certain 1-R-2-$R^1$-5/6-Y-indoles useful as intermediates in the preparation of the phthalides, the furo[3,4b]-pyridinones and the 2-indolylcarbonylbenzoic acids.

In the fourth of its composition of matter aspects, the invention relates to certain 2-(1-R-2-$R^1$-5/6-Y-indol-3-yl)carbonyl-X-benzoic acids useful as intermediates in the preparation of the phthalides.

In one of its process aspects, the invention relates to a process for producing 3-(1-R-2-$R^1$-5/6-Y-indol-3-yl)-3-(2-$R^2$-4-N-$R^3$-N-$R^4$-aminophenyl)-X-phthalides which comprises interacting the corresponding 2-(2-$R^2$-4-N-$R^3$-N-$R^4$-amino phenylcarbonyl)-X-benzoic acid with the appropriate 1-R-2-$R^1$-5/6-Y-indole.

In another of its process aspects, the invention relates to a process for producing 3-(1-R-2-$R^1$-5/6-Y-indol-3-yl)-3-(2-$R^2$-4-N-$R^3$-N-$R^4$-aminophenyl)-X-phthalides which comprises interacting the corresponding 2-(1-R-2-$R^1$-5/6-Y-indol-3-yl)carbonyl-X-benzoic acid with the appropriate 3-$R^2$-N-$R^3$-N-$R^4$-aniline.

In the third of its process aspects, the invention relates to a process for producing a compound selected from the group consisting of 7-(1-R-2-$R^1$-5/6-Y-indol-3-yl)-7-(2-$R^2$-4-N-$R^3$-N-$R^4$-aminophenyl)furo[3,4b]-pyridine-5(7H)-ones and 5-(1-R-2-$R^1$-5/6-Y-indol-3-yl)-5-(2-$R^2$-4-N-$R^3$-N-$R^4$-aminophenyl)furo[3,4b]-pyridine-7(5H)-ones and mixtures thereof which comprises interacting the corresponding 2/3-(1-R-2-$R^1$-5/6-Y-indol-3-yl)carbonylpyridine-3/2-carboxylic acid and mixtures thereof with the appropriate 3-$R^2$-N-$R^3$-N-$R^4$-aniline.

In the fourth of its process aspects, the invention relates to a process for producing a 3-(1-R-2-$R^1$-5/6-Y-indol-3-yl)-3-(2-$R^2$-4-N-$R^3$-N-$R^4$-aminophenyl)-5/6-COZ-phthalide which comprises interacting the appropriate 3-(1-R-2-$R^1$-5/6-Y-indol-3-yl)-3-(2-$R^2$-4-N-$R^3$-N-$R^4$-aminophenyl)-5/6-carboxyphthalide with the appropriate alkyl halide, alkyl sulfate, benzyl halide or substituted benzyl halide.

In the fIfth of its process aspects, the invention relates to a process for producing a 1-R-2-$R^1$-5/6-Y-indole which comprises interacting the corresponding 2-$R^1$-5/6-Y-indole with the appropriate $R^5$-O-alkyl halide.

In the sixth of its process aspects, the invention relates to a process for preparing a 2-(1-R-2-$R^1$-5/6-Y-indol-3-yl)carbonyl-X-benzoic acid which comprises interacting the corresponding 1-R-2-$R^1$-5/6-Y-indole with the appropriate X-phthalic anhydride.

The present invention provides in one of its article of manufacture aspects, a substrate for use in transfer imaging systems comprising a support sheet containing as a color-forming substance 3-(1-R-2-$R^1$-5/6-Y-indol-3-yl)-3-(2-$R^2$-4-N-$R^3$-N-$R^4$-aminophenyl)-X-phthalides.

The present invention provides in the second of its articles of manufacture aspects, a substrate for use in pressure-sensitive and thermal-responsive carbonless duplicating systems comprising a support sheet containing as a color-forming substance 3-(1-R-2-$R^1$-5/6-Y-indol-3-yl)-3-(2-$R^2$-4-N-$R^3$-N-$R^4$-aminophenyl)-X-phthalides.

The present invention provides in the third of its article of manufacture aspects, a substrate for use in transfer imaging comprising a support sheet containing as a color-forming substance a compound selected from the group consisting of a 7-(1-R-2-$R^1$-5/6-Y-indol-3-yl)-7-(2-$R^2$-4-N-$R^3$-N-$R^4$-aminophenyl)furo[3,4b]-pyridine-5(7H)-one and 5-(1-R-2-$R^1$-5/6-Y-indol-3-yl)-5-(2-$R^2$-4-N-$R^3$-N-$R^4$-aminophenyl)furo[3,4b]-pyridine-7(5H)-one and mixtures thereof.

The present invention provides in the fourth of its article of manufacture aspects, a substrate for use in pressure-sensitive and thermal-responsive carbonless duplicating systems comprising a support sheet containing as a color-forming substance a compound selected from the group consisting of 7-(1-R-2-R$^1$-5/6-Y-indol-3-yl)-7-(2-R$^2$-4-N-R$^3$-N-R$^4$aminophenyl)furo[3,4b]-pyridine-5(7H)-ones and 5-(1-R-2-R$^1$-5/6-Y-indol-3-yl)-5-(2-R$^2$-4-N-R$^3$-N-R$^4$-aminophenyl)furo[3,4b]pyridine-7(5H)-ones and mixtures thereof.

DETAILED DESCRIPTION INCLUSIVE OF THE PREFERRED EMBODIMENTS

More specifically, this invention in one of its composition of matter aspect resides in the novel 3-(1-R-2-R$^1$-phthalides having the formula

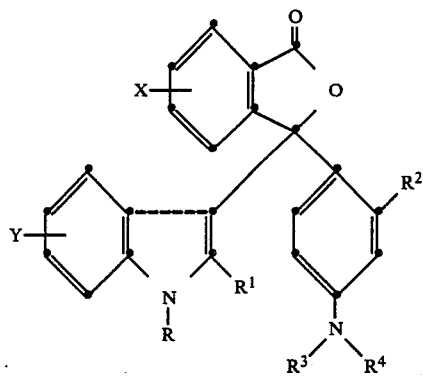

Formula I wherein: R represents alkylene-O-R$^5$ in which alkylene represents —C$_2$H$_4$— or —C$_3$H$_7$— and R$^5$ represents non-tertiary C$_1$ to C$_6$ alkyl, non-tertiary C$_2$ to C$_6$ alkenyl, phenyl or phenyl substituted by one or two of non-tertiary C$_1$ to C$_4$ alkyl, non-tertiary C$_1$ to C$_4$ alkoxy, halo, nitro, amino or amino substituted by one or two non-tertiary C$_1$ to C$_4$ alkyl; R$^1$ represents non-tertiary C$_1$ to C$_4$ alkyl or phenyl; R$^2$ represents hydrogen, halogen, non-tertiary C$_1$ to C$_4$ alkyl non-tertiary C$_1$ to C$_8$ alkoxy, dialkylamino in which alkyl is non-tertiary C$_1$ to C$_4$ alkyl, N-alkylamido in which alkyl is non-tertiary C$_1$ to C$_4$ alkyl, or trifluoromethyl; R$^3$ and R$^4$ independently represent non-tertiary C$_1$ to C$_8$ alkyl, alkylene-O-R$^5$, alkene-O-alkylene-O-R$^5$, benzyl, or benzyl substituted in the phenyl ring by one or two non-tertiary C$_1$ to C$_4$ alkyl, non-tertiary C$_1$ to C$_4$ alkoxy, halo or nitro; R$^3$ and R$^4$ taken together with the nitrogen represent piperidinyl pyrrolindinyl or morpholinyl; X represents hydrogen, nitro,

in which Z represents OR$^6$ wherein R$^6$ represents hydrogen, a non-tertiary C$_1$ to C$_{16}$ alkyl, benzyl or benzyl substituted in the phenyl ring by one or two of non-tertiary C$_1$ to C$_4$ alkyl, non-tertiary C$_1$ to C$_4$ alkoxy, halo or nitro, or one to four halogen; and Y represents hydrogen or one or two non-tertiary C$_1$ to C$_4$ alkyl, non-tertiary C$_1$ to C$_4$ alkoxy, halo or nitro.

Particular embodiments within the ambit of this composition of matter aspect are the novel 3-[1-(alkylene-O-R$^5$)-2-R$^1$-5/6-Y-indol-3-yl-3-(2-R$^2$-4-N-R$^3$-N-R$^4$-aminophenyl)-X-phthalides of Formula I wherein R is -alkylene-O-R$^5$ in which R$^5$ is non-tertiary C$_1$ to C$_6$ alkyl and R$^1$, R$^2$, R$^3$, R$^4$, X, Y and alkylene have the same respective meanings given in Formula I.

In the second of the composition of matter aspects, the invention resides in a novel compound selected from the group consisting of a 7-(1-R-2-R$^1$-5/6-Y-indol-3-yl)-7-(2-R$^2$-4-N-R$^3$-N-R$^4$-aminophenyl)furo[3,4-b]-pyridine-5(7H)-one having the formula

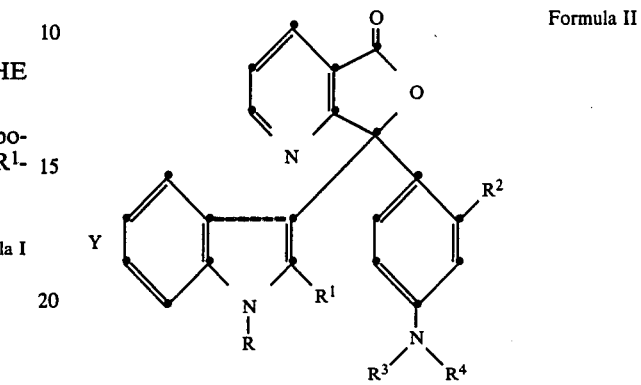

Formula II and a 5-(1-R-2-R$^1$-5/6-Y-indol-3-yl)-5-(2-R$^2$-4-N-R$^3$-N-R$^4$-aminophenyl)furo[3,4-b]-pyridine-7(5H)-one having the formula

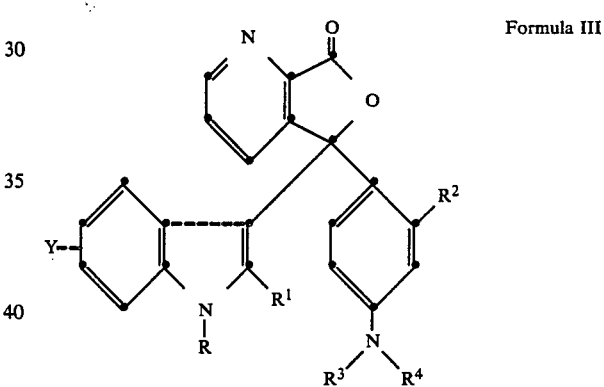

Formula III and mixtures thereof wherein: R represents alkylene-O-R$^5$ in which alkylene represents —C$_2$H$_4$— or —C$_3$H$_7$— and R$^5$ represents non-tertiary C$_1$ to C$_6$ alkyl, non-tertiary C$_2$ to C$_6$ alkenyl, phenyl or phenyl substituted by one or two of non-tertiary C$_1$ to C$_4$ alkyl, non-tertiary C$_1$ to C$_4$ alkoxy, halo, nitro, amino or amino substituted by one or two non-tertiary C$_1$ to C$_4$ alkyl; R$^1$ represents non-tertiary C$_1$ to C$_4$ alkyl or phenyl; R$^2$ represents hydrogen, halogen, non-tertiary C$_1$ to C$_4$ alkyl non-tertiary C$_1$ to C$_8$ alkoxy, dialkylamino in which alkyl is non-tertiary C$_1$ to C$_4$ alkyl, N-alkylamido in which alkyl is non-tertiary C$_1$ to C$_4$ alkyl, or trifluoromethyl; R$^3$ and R$^4$ independently represent non-tertiary C$_1$ to C$_4$ alkyl, alkylene-O-R$^5$, alkene-O-alkylene-O-R$^5$, benzyl, or benzyl substituted in the phenyl ring by one or two non-tertiary C$_1$ to C$_4$ alkyl, non-tertiary C$_1$ to C$_4$ alkoxy, halo or nitro; R$^3$ and R$^4$, taken together with the nitrogen represent piperidinyl pyrrolindinyl of morpholinyl; and Y represents hydrogen or one or two non-tertiary C$_1$ to C$_4$ alkyl, non-tertiary C$_1$ to C$_4$ alkoxy, halo or nitro.

Particular embodiments within the ambit of the second composition of matter aspect are the novel 7-(1-R-2-R$^1$-5/6-Y-indol-3-yl)-7-(2-R$^2$-4-N-R$^3$-N-R$^4$-aminophenyl)furo[3,4-b]-pyridine-5(7H)-ones of Formula II and the 5-(1-R-2-R$^1$-5/6-Y-indol-3-yl)-5-(2-R$^2$-4-N-R$^3$-

N-$R^4$-aminophenyl)furo[3,4-b]-pyridine-7(5H)-ones of Formula III wherein R is alkylene-O-$R^5$ in which $R^5$ is non-tertiary $C_1$ to $C_6$ alkyl and $R^1$, $R^2$, $R^3$, $R^4$, Y and alkylene have the same respective meanings given in Formulas II and III.

In the third of its composition of matter aspects, the invention resides in a 1-R-2-$R^1$-5/6-Y-indoles having the formula

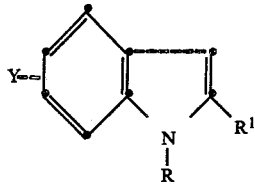

FORMULA IV wherein: R represents alkylene-O-$R^5$ in which alkylene represents —$C_2H_5$— or —$C_3H_7$—; $R^5$ represents non-tertiary $C_1$ to $C_6$ alkyl, non-tertiary $C_2$ to $C_6$ alkenyl, phenyl or phenyl substituted by one or two of non-tertiary $C_1$ to $C_4$ alkyl, non-tertiary $C_1$ to $C_4$ alkoxy, halo, nitro, amino or amino substituted by one or two non-tertiary $C_1$ to $C_4$ alkyl; $R^1$ represents non-tertiary $C_1$ to $C_4$ alkyl or phenyl; $R^2$ represents hydrogen, halogen, non-tertiary $C_1$ to $C_4$ alkyl non-tertiary $C_1$ to $C_8$ alkoxy, dialkylamino in which alkyl is non-tertiary $C_1$ to $C_4$ alkyl, N-alkylamido in which alkyl is non-tertiary $C_1$ to $C_4$ alkyl, or trifluoromethyl; $R^3$ and $R^4$ independently represent non-tertiary $C_1$ to $C_8$ alkyl, or alkene-O-alkylene-O-$R^5$, alkylene-O-$R^5$, benzyl, benzyl substituted in the phenyl ring by one or two non-tertiary $C_1$ to $C_4$ alkyl, non-tertiary $C_1$ to $C_4$ alkoxy, halo or nitro or $R^3$, and $R^4$ taken together with the nitrogen represent piperidinyl, pyrrolindinyl or morpholinyl; X represents hydrogen, nitro,

in which Z represents $OR^6$ wherein $R^6$ represents hydrogen, a non-tertiary $C_1$ to $C_{16}$ alkyl, benzyl or benzyl substituted in the phenyl ring by one or two of non-tertiary $C_1$ to $C_4$ alkyl, non-tertiary $C_1$ to $C_4$ alkoxy, halo or nitro, or one to four halogen; and Y represents hydrogen or one or two non-tertiary $C_1$ to $C_4$ alkyl, non-tertiary $C_1$ to $C_4$ alkoxy, halo or nitro.

In the fourth of its composition of matter aspects, the invention resides in a 2-(1-R-2-$R^1$-5/6-Y-indol-3-yl) carbonyl-X-benzoic acid having the formula Formula V

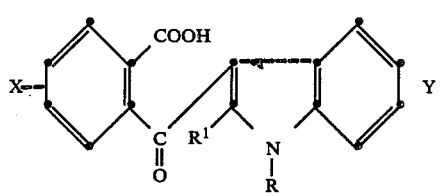

wherein: R represents alkyleee-O-$R^5$ in which alkylene represents —$C_2H_4$— or —$C_3H_7$— and $R^5$ represents non-tertiary $C_1$ to $C_6$ alkyl, non-tertiary $C_2$ to $C_6$ alkenyl, phenyl or phenyl substituted by one or two of non-tertiary $C_1$ to $C_4$ alkyl, non-tertiary $C_1$ to $C_4$ alkoxy, halo, nitro, amino or amino substituted bv one or two non-tertiary $C_1$ to $C_4$ alkyl; $R^1$ represents non-tertiary $C_1$ to $C_4$ alkyl or phenyl; $R^2$ represents hydrogen, halogen, non-tertiary $C_1$ to $C_4$ alkyl non-tertiary $G_1$ to $C_8$ alkoxy, dialkylamino in which alkvl is non-tertiary $C_1$ to $C_4$ alkyl, N-alkylamido in which alkyl is non-tertiary $C_1$ to $C_4$ alkyl, or trifluoromethyl; $R^3$ and $R^4$ independently represent non-tertiary $C_1$ to $C_8$ alkyl, or alkene-O-alkylene-O-$R^5$, alkylene-O-$R^5$, benzyl, benzyl substituted in the phenyl ring by one or two non-tertiary $C_1$ to $C_4$ alkyl, non-tertiary $C_1$ to $C_4$ alkoxy, halo or nitro; or $R^3$, and $R^4$ taken together with the nitrogen represent piperidinyl, pyrrolindinyl or morpholinyl; X represents hydrogen, nitro,

in which Z represents —$OR^6$ wherein $R^6$ represents hydrogen; and Y represents hydrogen or one or two non-tertiary $C_1$ to $C_4$ alkyl, non-tertiary $C_1$ to $C_4$ alkoxy, halo or nitro.

In one of its process aspects, the invention sought to be patented resides in the process for preparing a 3-(1-R-2-$R^1$-5/6-Y-indol-3-yl)-3-(2-$R^2$-4-N-$R^3$-N-$R^4$-aminophenyl)-X-phthalide according to Formula I which comprises in interacting the corresponding 2-(2-$R^2$-4-N-$R^3$-N-$R^4$-aminophenylcarbonyl)-X-benzoic acid having the structural formula Formula VI

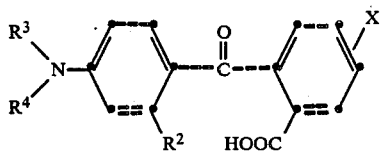

with the appropriate 1-R-2-$R^2$-5/6-Y-indole of Formula IV in which R, $R^1$, $R^2$, $R^3$, $R^4$, X and Y have the same respective meanings given in Formula I.

In the second of its process aspects, the invention sought to be patented resides in the process for preparing a 3-(1-R-2-$R^1$-5/6-Y-indol-3-yl)-3-(2-$R^2$-4-N-$R^3$-N-$R^4$-aminophenyl)-X-phthalide according to Formula I which comprises interacting the corresponding 2-(1-R-2-$R^1$-5/6-Y-indol-3-yl)carbonyl-X-benzoic acid having the structural Formula V with the appropriate 3-$R^2$-N-$R^3$-N-$R^4$-aniline having the structural formula Formula VII

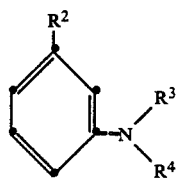

in which R, $R^1$, $R^2$, $R^3$, $R^4$, X and Y have the same respective meanings given in Formula I.

In the third of its process aspects, the invention sought to be patented resides in the process for preparing a compound selected from the group consisting of 7-(1-R-2-$R^1$-5/6-Y-indol-3-yl)-7-(2-$R^2$-4-N-$R^3$-N-$R^4$-aminophenyl)furo[3,4-b-pyridine-5(7H)ones and 5-(1-R-2-$R^1$-5/6-Y-indol-3-yl)-5-(2-$R^2$-4-N-$R^3$-N-$R^4$-aminophenyl)furo[3,4-b]-pyridine-7(5H)ones according to Formulas II and III and mixtures thereof which comprises in interacting the corresponding 2-(1-R-2-$R^1$-

5/6-Y-indol-3-yl)carbonylpyridine-3-carboxylic acid having the formula

FORMULA VIII

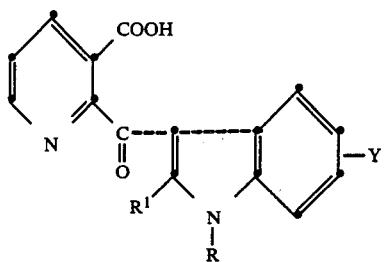

or 3-(1-R-2-R$^1$-5/6-Y-indol-3-yl)carbonylpyridine-2-carboxylic acid having the formula

FORMULA IX

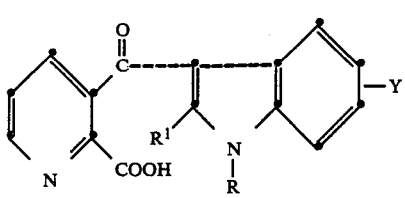

and mixtures thereof with appropriate 3-R$^2$-N-R$^3$-N-R$^4$-aniline of Formula VI in which R, R$^1$, R$^2$, R$^3$, R$^4$, and Y have the same respective meanings given in Formulas II and III.

In the fourth of its process aspects, the invention sought to be patented resides in the process for preparing a 3-(1-R-2-R$^1$-5/6-Y-indol-3-yl)-3-(2-R$^2$-4-N-R$^3$-N-R$^4$-amino-phenyl)-5/6-COZ-phthalide in which Z represents R$^6$O— according to Formula I which comprises interacting the corresponding 3-(1-R-2-R$^1$-5/6-Y-indol-3-yl)-3-(2-R$^2$-4-N-R$^3$-N-R$^4$-aminophenyl)- 5/6-COOH-phthalide of Foruula I with the appropriate alkyl halide, alkyl sulfate, benzyl halide or substituted benzyl halide having the formula R$^6$-A which R$^6$ represents non-tertiary C$_1$ to C$_{16}$ alkyl, benzyl or benzyl substituted in the phenyl ring by one or two of non-tertiary C$_1$ to C$_4$ alkyl, non-tertiary C$_1$ to C$_4$ alkoxy, halo or nitro and A represents halide or sulfate.

In the fifth of its process aspects, the invention sought to be patented resides in the process for preparing a 1-R-2-R$^1$-5/6-Y-indole of Formula IV which comprises interacting an 2-R$^1$-5/6-Y-indole with an appropriate R$^5$-O-alkyl halide wherein R, R$^1$R$^5$ and Y have the same respective meanings given in Formula IV.

In the sixth of its process aspects, the invention sought to be patented resides in the process for preparing a 2-(1-R-2-R$^1$-5/6-Y-indol-3-yl)carbonyl-X-benzoic acid according to Formula V which comprises interacting a 1-R-2-R$^1$-5/6-Y-indole of Formula IV with an appropriate X-phthalic anyhdride having the formula Formula X

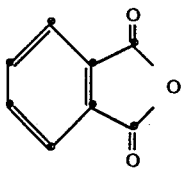

wherein R, R$^1$, X and Y have the same respective meanings given in Formula V.

In one of its article of manufacture aspects, the invention sought to be patented resides in a substrate for use in transfer imaging comprising a support sheet coated with a layer containing as a color-forming substance a 3-(1-R-2-R$^1$-5/6-Y-indol-3-yl)-3-(2-R$^2$-4-N-R$^3$-N-R$^4$-aminophenyl)-X-phthalide of Formula I wherein R, R$^1$, R$^2$, R$^3$, R$^4$, X and Y have the same respective meanings given in Formula I.

In a second its article of manufacture aspects, the invention sought to be patented resides in a substrate for use in a pressure-sensitive or thermal-responsive marking system comprising a support sheet coated with a layer contaIning as a color-forming substance a 3-(1-R-2-R$^1$-5/6-Y-indol-3-yl)-3-(2-R$^2$-4-N-R$^3$-N-R$^4$-aminophenyl)-X-phthalide according to Formula I wherein R, R$^1$, R$^2$, R$^4$, X and Y have the same respective meanings given in Formula I.

In a particular embodiment in accordance with its second article of manufacture aspects, the invention sought to be patented resides in a pressure-sensitive transfer sheet, adapted for use with a receiving sheet having an electron-accepting layer, comprising a support sheet coated on one side with a layer of pressure-rupturable microcapsules, said microcapsules containing a liquid solution of a color-forming substance comprising at least one compound having Formula I.

Another embodiment in accordance with its second article of manufacture aspect, resides in a thermal-responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

In a third of its article of manufacture aspects, the invention sought to be patented resides in a substrate for use in transfer imaging comprising a support sheet coated with a layer containing as a color-forming substance a compound selected from the group consisting of a 7-(1-R-2-R$^1$-5/6-Y-indol-3-yl)-7-(2-R$^2$-4-N-R$^3$-N-R$^4$-aminophenyl)furo[3,4-b]-pyridine-5(7H)-one of Formula II and 5-(1-R-2-R$^1$-5/6-Y-indol-3-yl)-5-(1-R$^2$-4-N-R$^3$-N-R$^4$-aminophenyl)furo[3,4-b]pyridine-7(5H)-one of Formula III or mixtures thereof wherein R, R$^1$, R$^2$, R$^3$, R$^4$, and Y have the same respective meanings given in Formulas II and III.

In a fourth of its article of manufacture aspects, the invention sought to be patented resides in a substrate for use in a pressure-sensitive or thermal-responsive marking system comprising a support sheet coated with a layer contaIning as a color-forming substance a compound selected from the group consisting of a 7-(1-R-2-R$^1$-5/6-Y-indol-3-yl)-7-(2-R$^2$-4-N-R$^3$-N-R$^4$-amino-phenyl)furo[3,4-b]pyridine-5(7H)-one according to Formula II and 5-(1-R-2-R$^1$-5/6-Y-indol-3-yl)-5-(2-R$^2$-4-N-R$^3$-N-R$^4$-aminophenyl)furo[3,4-b]-pyridine-7(5H)-one according to Formula III or mixtures thereof wherein R, R$^1$, R$^2$, R$^3$, R$^4$, and Y have the same respective meanings given in Formulas II and III.

In a particular embodiment in accordance with its fourth article of manufacture aspect, the invention sought to be patented resides in a pressure-sensitive transfer sheet, adapted for use with a receiving sheet having an electron-accepting layer, comprising a support sheet coated on one side with a layer of pressure-rupturable microcapsules; said microcapsules containing a liquid solution of a color-forming substance comprising at least one compound having Formula II or Formula III or a mixture thereof.

Another embodiment in accordance with the fourth article of manufacture aspect, resides in a thermal-responsive record material comprising a support sheet coated on one side with a layer containing a mixture comprising at least one color-forming compound having Formula II or Formula III or a mixture there of and an acidic developer arranged such that application of heat will produce a mark-forming reaction between the color-forming compound and the acidic developer.

As use herein the terms "non-tertiary $C_1$ to $C_8$ alkyl" and "non-tertiary $C_1$ to $C_{16}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, n-dodecyl and the like.

The term "non-tertiary $C_1$ to $C_4$ alkoxy" includes saturated acyclic, straight or branched-chained groups such as methoxy, ethoxy, propoxy, isopropoxy, butoxy, sec-butoxy and isobutoxy.

As used herein the terms "halo" and "halogen" include chloro, fluoro, bromo and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

The term "$C_2$ to $C_6$ alkenyl" includes ethenyl (or vinyl), 2-propenyl (or allyl), 1-methylethenyl (or isopropenyl), 2-methyl-2-propenyl, 2-methyl-1-propenyl, 2-butenyl, 3-butenyl, 3-pentenyl, 2-pentenyl, 3-methyl-2-butenyl, 2-methyl-1-butenyl (isoamylenyl), 3-methyl-1-butenyl, 1-hexenyl, 2-hexenyl, and 3-hexenyl.

The compounds of Formulas I, II, and III hereinabove are essentially colorless in the depicted lactone form. When contacted with a color developer such as those conventionally employed in carbonless duplication systems which are generally acidic in nature, the compounds of Formulas I, II, and III develop purple, blue, and cyan-colored images. Illustrative of specific examples of these color developers are clay minerals such as acid clay, active clay, attapulgite and silton clays; organic acids such as tannic acid, gallic acid, propyl gallate and so forth; acid polymers such as phenol-formaldehyde resins, phenol acetylene condensation resins, condensates between an organic carboxylic acid having at least one hydroxy group and formaldehyde, as so forth; metal salts of aromatic carboxylic acids such as zinc salicylate, tin salicylate, zinc 2-hydroxy naphthoate, zinc 3,5-di-tertiary-butyl salicylate, oil soluble metal salts of phenol-formaldehyde novolak resins and so forth. These color developers are also useful in transfer imaging systems. The developed images are very insensitive to light, are of good tinctorial strength, possess excellent xereographic copiability and enhanced solubility in common organic solvents. The compounds are thus highly suitable for use as colorless precursors, that is, color-forming substances in pressure-sensitive carbonless duplicating systems. The compounds of Formulas I, II, and III can be used alone as color formers to produce images which are readily copiable, or can be used as toners to admixture with other color formers to produce images of neutral shade which desirably are readily copiable by xerographic means.

The compounds of Formulas I, II, and III may be incorporated into transfer imaging systems which refer to office based systems suitable for making photocopies. One such system is disclosed in U.S. Pat. No. 4,399,209. In this system the color-forming phthalides of Formulas I, II, and III are microencapsulated together with a photoinitiator in a photo-sensitive composition in pressure rupturable capsules. The microcapsules are then coated onto a surface of a substrate. Images are formed by image-wise exposing the encapsulated bearing substrate to actinic radiation and rupturing the capsules in the presence of a developer to obtain an image.

The compounds of this invention may be incorporated in any of the commercially-accepted systems known in the carbonless duplicating art. A typical technique for such applications is as follows. Solutions containing one or more colorless compounds of Formulas I, II, and III optionally in admixture with other color formers, in suitable solvents are microencapsulated by well-known procedures, for example, as described in U.S. Pat. Nos. 3,369,649, 3,429,827, and 4,000,087. The microcapsules are coated on the reverse side of a sheet with the aid of a suitable binder and the coated transfer sheet is then assembled in a manifold with the microcapsule coated side in contact with a receiving sheet coated with an electron-accepting substance, for example, silton clay or a phenolic resin. Application of pressure to the manifold such as that exerted by a stylus, typewriter or other form of writing or printing causes the capsules on the reverse side to rupture. The solution of the color formers released from the ruptured microcapsules flows to the receiving sheet and on contact with the acidic medium thereon forms purple, blue, and cyan-colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formulas I, II, and III are intimately mixed with an acidic developer, for example, bisphenol A, of the type generally employed in thermal papers such as described in U.S. Pat. No. 3,539,375, that is, papers which produce a colored image when contacted with a heated stylus or heated type heating of the mixture produces a colored image of varying shades from purple to cyan depending on the particular compound of the invention employed. The ability of the compounds of Formulas I, II, and III to form a deep color when heated in admixture with an acidic developer such s bisphenol A, makes them useful in thermal paper marking systems, either where an original or a duplicate copy is prepared by contacting the thermal paper with a heated stylus or heated type in any of the methods generally known in the art.

The best mode contemplated by the inventors of carrying out this invention will now be described so as to enable any person skilled in the art to which it pertains to make and use the same.

In accordance with one of the aforementioned process aspects of this invention, the compounds of Formula I are obtained by reacting one molecular proportion of a 2-(2-$R^2$-4-N-$R^3$-N-$R^4$-aminophenyl)carbonyl-X-benzoic acid of Formula VI with one molecular proportion of a 1-R-2-$R^1$-5/6-Y-indole of Formula IV. The reaction is conveniently carried out in a dehydrating solvent, for example, an anhydride of a $C_2$ to $C_5$ alkanoic acid such as acetic anhydride in the approximate temperature range of 60° C. to reflux from approximately one hour to approximately twenty hours. The phthalides of Formula I thus obtained can be isolated by several methods. One such method of isolation is to pour the reaction mixture into ice water or a mixture of ice and water and dilute aqueous base such as ammonium hydroxide and to filter the phthalides from the mixture. An alternative method of isolation is to pour the reaction mixture into a mixture of water immiscible organic liquid in which the phthalides are soluble such as toluene and water or a dilute base such as ammonium hydroxide solution. The organic liquid layer containing the phthalides is separated from the aqueous layer and the phthalide is isolated by removing the organic liquid by evaporation or distillation. The phthalide, once isolated, can be purified by conventional means such as trituration or recrystallization from a suitable solvent and then collection by filtration. Purification can also be effected by column chromatography. The phthalide to be purified is dissolved in a suitable organic liquid or combination of organic liquids and the solution is passed through a chromatography column which has been packed with a suitable substrate, for example, silica gel, cellulose, alumina and the like. Numerous fractions are collected and analyzed to determine fraction(s) containing the desired phthalide. The fraction(s) which contain the desired product are then combined (if more than one) and concentrated to obtain the phthalide which is then collected by filtration.

In accordance with the second of the aforementioned process aspects of the invention, the compounds of Formula I are obtained by reacting one molecular proportion of a 2-(1-R-2-$R^1$-5/6-Y-indol-3-yl)carbonyl-X-benzoic acid of Formula V with one molecular proportion of a 3-$R^2$-N-$R^3$-N-$R^4$-aniline of Formula VII. This process is carried out in a manner identical to the process aspect discussed directly above.

The 3-(1-R-2-$R^1$-5/6-indol-3-yl)-3-(2-$R^2$-4-N-$R^3$-N-$R^4$-aminophenyl)-5/6-$R^6$OOC-phthalides of Formula I in which $R^6$ is a non-tertiary $C_1$ to $C_{16}$ alkyl, benzyl or benzyl substituted in the benzene ring by one or two of a non-tertiary $C_1$ to $C_4$ alkyl, non-tertiary $C_1$ to $C_4$ alkoxy, halo or nitro are obtained by interacting a 3-(1-R-2-$R^1$-5/6-Y-indol-3-yl)-3-(2-$R^2$-4-N-$R^3$-N-$R^4$-aminophenyl)-5/6-COOH-phthalide with an appropriate alkylating agent, for example, dimethyl sulfate, diethyl sulfate, ethyl iodide, butyl bromide, allyl chloride, octyl bromide, hexadecyl bromide, benzyl bromide or a substituted benzyl halide in an inert dilutent, for example, acetone or N,N-dimethylformamide in the presence of an alkali metal salt, for example, sodium hydroxide, sodium carbonate, potassium hydroxide or potassium carbonate. The reaction is conveniently carried out at a temperature in the range of 10° C. to 100° C. for approximately one to three hours. The phthalide thus obtained is isolated by adding the reaction mixture to water with subsequent extraction into and subsequent isolation from an aromatic organic liquid, for example, benzene or toluene. The organic layer is separated, dried over a suitable drying agent, followed by evaporation of the organic liquid leaving the phthalide as a residue. The product once isolated can be purified by conventional means such as trituration or recrystallization from a suitable organic liquid.

In accordance with another of the aforementioned process aspects of this invention, the compounds of Formulas II and III are obtained by reaction one molecular proportion of a pyridinecarboxylic acid of Formula VIII or IX or mixtures thereof and an aniline of Formula VII in the anhydride of an alkanoic acid having 2 to 5 carbon atoms such as acetic anhydride at a temperature in the range of 60° C. to reflux for from approximately one hour to approximately twenty hours. The product thus obtained can be isolated by pouring the reaction mixture into an aqueous base such as ammonium hydroxide, sodium hydroxide, sodium carbonate or sodium bicarbonate and the product extracted with a water immisible organic liquid such as toluene or chlorobenzene followed by evaporation of the organic liquid leaving the product as a residue. The product once isolated, can be purified by conventional means such as trituration or recrystallization from a suitable solvent. Purification can also be effected by column chromatography. The compound to be purified is dissolved in a suitable organic liquid or combination of organic liquids and the solution is passed through a chromatography column which has been packed with a suitable substrate, for example, silica gel, cellulose, alumina and the like. Numerous fractions are collected and analyzed to determine fraction(s) containing the desired compound. The fraction(s) which contain the desired product are then combined (if more than one) and concentrated to obtain the compound which is then collected by filtration.

The novel 2-(1-R-2-$R^1$-5/6-Y-indol-3-yl)carbonylbenzoic acids of Formula V of this invention are readily obtained by conventional procedures well known in the art such as the ones described in U.S. Pat. Nos. 4,094,877 and 4,168,378. The benzoic acids of Formula V are prepared by interacting a X-phthalic anhydride of Formula X with a 1-R-2-$R^1$-5/6-Y-indole of Formula IV in a dilutent, such as a $C_2$ to $C_5$ alkanoic acid, for example, acetic acid at a temperature of from 60° C. to the reflux temperature of the alkanoic acid. The desired benzoic acids are obtained by cooling the reaction mixture to ambient temperature and collecting the product by filtration. The benzoic acids can be purified by conventional means but are generally dried and used as is.

The requisite 2-(2-$R^2$-4-N-$R^3$-N-$R^4$-aminophenyl)carbonyl-X-benzoic acids of Formula VI required in the practice of this invention belong to a known class of compounds and are readily obtained by conventional procedures well known in the art such as the ones described in U.S. Pat. Nos. 3,812,146 and 4,322,352.

The pyridine carboxylic acids of Formulas VIII and IX which are novel can be prepared in accordance with the procedures described in the literature, for example, as disclosed in U.S. Pat. No. 3,936,564, issued Feb. 3, 1976; U.S. Pat. No. 3,775,424, issued Nov. 27, 1973; Japanese Patent No. 73/8727, published Mar. 17, 1973; Japanese Patent No. 73/3205, published Jan. 30, 1973; and Japanese Patent No. 73/8729, published Mar. 17, 1973, for the preparation of similar compounds, i.e. by reacting an anhydride having the formula

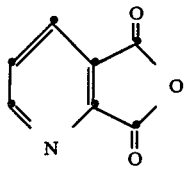

Formula XI with an appropriate indole of the Formula IV. The pyridine carboxylic acids of Formulas VIII an IX can be prepared by simply heating the reactants together in an inert organic liquid at a temperature in the range 80° to 150° C.

It will, of course, be appreciated that reaction of the inherently unsymmetrical anhydride of Formula XI with an indole of Formula IV can produce isomers or a mixture of isomers of indolylcarbonylpyridinecarboxylic acids of Formulas VIII and IX. For example, reaction of 2,3-pyridinedicarboxylic anhydride of Formula XI with an indole of Formula IV can produce either a 2-(indolyl)carbonylpyridine-3-carboxylic acid of Formula VIII or a 3-(indolyl)carbonylpyridine-2-carboxylic acid of Formul IX or a mixture of these isomers. It will, of course, be appreciated that the ratio of isomers obtained will depend on various reaction conditions such as temperutures, solvent, and the relative solubility of the isomers in the reaction medium. Ordinarily, when carried out as described herein, the reaction produces a mixture of isomers with the 2-(indolyl)carbonylpyridine-3-carboxylic acid predominating in the isolated product. If desired, the mixture of isomers can be separated by conventional means such as selective precipitation at different pH, fractional crystallization or chromatography and each of the individual isomers can then be reacted with an appropriate 3-$R^2$-N-$R^3$-N-$R^4$-aniline of Formula VII to produce a furo[3,4-b]pyridine-5(7H)-one of Formula II and a furo[3,4-b]pyridine-7(5H)-one of Formula III, respectively. It is generally preferred however, to simply react the isolated mixture of isomeric indolylcarbonyl-pyridinecarboxylic acids of Formulas VIII and IX with an aniline to produce an isomer mixture of furopyridinones of Formulas II and III which can be separated by conventional means if desired. However, since both isomers are useful as color formers, it is economically advantageous to simply use the isolated mixture of isomers in the practice of this invention.

The 1-$R^5$-O-alkylene-2-$R^1$-5/6-Y-indoles required as intermediates of the phthalides of Formula I and the 2-(1-R-2-$R^1$-5/6-Y-indol-3-yl)carbonyl-X-benzoic acids of Formula V are prepared by interacting approximately one molecular proportion of a 2-$R^1$-5/6-Y-indole with approximately one molecular proportion of a $R^5$-alkylene-Z alkylating agent. The reaction is conveniently carried out in an organic liquid such as dimethylsulfoxide in the presence of an alkali metal hydroxide, for example, potassium hydroxide or sodium hydroxide at a temperature in the range of 35° C. to 95° C. The desired indole is isolated by pouring the reaction mixture into a water immisible organic liquid such as toluene and the resulting mixture is washed with water and saturated aqueous sodium chloride solution. The organic liquid is removed from the resulting layer by distillation at reduced pressure to obtain the desired indole which is an oil. The indoles may be purified by conventional methods such as distillation or column chromatography.

It will, of course, be appreciated that reaction of an unsymmetrically substituted phthalic anhvdride with an indole or a N,N-disuhstituted aniline can produce isomers or a mixture of isomers of 2-(indolyl)carbonylbenzoic acids or 2-(4-disubstituted aminophenyl)carbonylbenzoic acids. For example, reaction of a -substituted phthalic anhydride with an indole or a N,N-disubstituted benzoic acid can produce either a 4- or 5-substituted-2-(indolyl- or 4-disubstituted aminophenyl)carbonylbenzoic acid or a mixture thereof. These mixtures of isomeric 2-(indolyl- or 4-disubstituted aminophenyl)-carbonylbenzoic acids can be separated by conventional means such as fractional crystallization or chromatography. Alternatively, the isomeric mixtures can be reacted with 3-$R^2$-N-$R^3$-N-$R^4$-anilines or 1-R-2-$R^1$-5/6-Y-indoles to produce isomeric mixtures of phthalides of Formula I. Thus, reaction of a mixture of 4- and 5-substituted 2-(indolyl- or 4-disubstituted aminophenyl)carbonylbenzoic acids with a 3-$R^3$-N-$R^3$-N-$R^4$-anilines or a 1-R-2-$R^1$-5/6-Y-indole will produce a mixture of 5- and 6-substituted phthalides. The mixtures of phthalides can, if desired, be separated by conventional means or simply and preferably used as mixtures in the practice of this invention. Throughout this application where the possibility of different isomeric products being formed is present, the nomenclature 4/5, 5/6 and so forth is adopted meaning the product obtained or claimed is a mixture of the isomers.

The molecular structures of the compounds were assigned on the basis of the modes of synthesis and a study of their infrared and nuclear magnetic resonance spectra.

The following examples will further illustrate the invention without, however, limiting it thereto.

Preparation of Indoles

EXAMPLE A

With stirring 75.0 g of 2-methylindole was dissolved in 300.0 ml of dimethylsulfoxide and while maintaining a temperature of approximately 20° C. by using an ice bath, 54.4 g of ground potassium hydroxide was added slowly to the solution. The ice bath was removed and the reaction mixture was stirred for approximately one hour at ambient temperature. The resultant mixture was cooled to approximately 8° C. and 91.7 g of 1-chloro-2-methoxyethane was added while maintaining approximately 8° C. After the addition was complete, the reaction mixture was heated to approximately 70° C. An exotherm occurred which required cooling. The temperature was maintained at approximately 70° C. for approximately six hours. The reaction mixture was cooled to room temperature and toluene was added. The toluene mixture was filtered to remove the sodium chloride and other insolubles. The toluene solution was washed three times with saturated aqueous sodium chloride solution and the toluene was distilled from the solution to obtain 102.45 g of a pale yellow-green-colored oil which analyzed by gas chromatography to be 95 percent 1-(2-methoxyethyl)-2-methyl indole (Formula IV: R=$CH_3OC_2H_4$; $R^1$=$CH_3$; Y=H). Significant infrared maxima appeared at 1130 (C-O;s)$cm^{-1}$. The nuclear magnetic resonance spectrum was consistent with the assigned structure.

EXAMPLE B

Following the procedure described in Example A above, 75.0 g of 2-methylindole, 54.4 g of ground potassium hydroxide and 94.0 ml of 1-chloro-2-ethoxyethane were interacted in 300.0 ml of dimethylsulfoxide to obtain 126.1 g of a brown-colored oil containing 87.1 percent of 1-(2-ethoxyethyl)-2-methylindole (Formula IV: R=$C_2H_5OC_2H_4$; $R^1$=$CH_3$; Y=H). Significant infrared maxima appeared at 1130 (C—O;s)cm$^{-1}$.

EXAMPLE C

Proceeding in a manner similar to that described in Example A above, 18.82 g of 2-methylindole, 16.0 g of ground potassium hydroxide and 10.6 g of 1-chloro-2-vinyl-oxyethane were interacted to obtain 18.3 g of a pale yellow-orange colored oil which contained 84.5 percent of 1-(2-vinyloxyethyl)-2-methylindole (Formula IV: R=$CH_2$=$CHOC_2H_4$; $R^1$=$CH_3$; Y=H). Significant infrared maxima appeared at 1645 (CH=CH;s) and 1210 (C—O;s)cm$^{-1}$.

EXAMPLE 1

A mixture consisting of 16.5 g 2-(2-methyl-4-diethylaminophenylcarbonyl)benzoic acid (94.6 percent active), 11.0 g of 1-(2-methoxyethyl-2-methylindole) (91.8 percent active) and 75.0 ml of acetic anhydride was heated at approximately 70° C. for approximately two and one-half hours. After cooling to ambient temperature, 50.0 ml of isopropyl alcohol was added and the resulting solution was poured into 800.0 ml of 5 percent aqueous ammonium hydroxide solution. The gummy, tar-like solid which formed was dissolved in toluene and the resulting toluene layer was separated from the water layer. The toluene layer was washed with water and evaporated to dryness to obtain a gummy residue. The residue was triturated with hexane. The resulting slurry was filtered and the solid dried to obtain 19.2 g of 3-[1-(2methoxyethyl)-2-methylindol-3-yl]-3-(2-methyl-4-diethylaminophenyl)phthalide (Formula I: R=$CH_3OC_2H_4$; $R^1$=$R^2$=$CH_3$; $R^3$=$R^4$=$C_2H_5$; X=Y=H), a pale pink solid which melted at 145°-148° C. Significant infrared spectrum maxima appeared at 1755 (C=O;s)cm$^{-1}$ and 1125 (C—O;s)cm$^{-1}$. The nuclear magnetic resonance spectrum was in accord with the assigned structures. A toluene solution of the product spotted on an acidic clay or a phenolic resin coated paper developed a cyan-colored image.

EXAMPLE 2

A mixture of 10.12 g 2-[1-(2-methoxyethyl)-2-indol-3-yl]carbonylbenzoic acid, 5.0 g of 3-methyl-N,N-diethylaniline and 0.0 ml of acetic anhydride was heated at approximately 85° C. overnight. After cooling to room temperature, the solution was slowly poured into ice water. The tar-like solid which formed was extracted with toluene. After separating from the water later, the resulting toluene layer was evaporated to dryness. The resulting gummy residue was dissolved in ethyl acetate:toluene, (V/V) 2:23 and the resulting solution was passed through a silica gel packed chromatography column eluting the column with ethyl acetate:toluene and collecting eleven fractions. Fractions 1, 9, 10, and 11 were discarded. Fractions 2, 3, 4, and 5 were combined as well as fractions 6, 7, and 8. Each of the combinations were evaporated to dryness leaving a gummy residue. The residues were refluxed in hexane, cooled to ambient temperatures and allowed to sit overnight. The solids from the combination of fractions 2, 3, 4, and 5 were collected by filtration and air dried to obtain 3.97 g of 3-[1-(2-methoxyethyl)-2-methylindol-3-yl]-3-(2-methyl-4-diethylaminophenyl)phthalide, (Formula I: R=$CH_3OC_2H_4$; $R^1$=$R^2$=$CH_3$; $R^3$=$R^4$=$C_2H_5$; X=Y=H) cream-colored solid which melted at 140°-143° C. The solid obtained from the combination of fractions 6, 7, and 8 weighed 0.4 g and was the same product. A significant infrared maxims appeared at 1755 (C=O;s)cm$^{-1}$. A toluene solution of the product spotted on an acidic clay or a phenolic resin coated paper developed a cyan-colored image.

EXAMPLE 3

A mixture of 14.5 g of 2-(2-methyl-4-diethylaminophenyl)carbonylbenzoic acid (68.5 percent active). 9.0 g of 1-(2-ethoxyethyl) 2-methylindole and 60.0 ml acetic anhydride was maintained at approxmmately 70° C. for approximately three hours. After cooling to ambient temperature, the reaction solution was poured slowly into a mixture of toluene and 5 percent aqueous ammonium hydroxide. The toluene layer was separated and evaporated to dryness to obtain a gummy residue. The residue was triturated with hexane and the solid which separated was isolated by filtration. The solid was re-slurried in 300.0 ml of hot hexane, filtered, and dried to obtain 11.5 g of 3-[1-(2-ethoxyethyl)-2-methylindol-3-yl]-3-(2-ethyl-4-diethylaminophenyl) phthalide (Formula I: R=$C_2H_5OC_2H_4$; $R^1$=$R^2$=$CH_3$; $R^3$=$R^4$=$C_2H_5$; X=Y=H), a pale pink-colored solid which melted at 156°-158° C. Significant infrared maxima appeared at 1765 (C=O;s) and 1120 (C—O;s)cm$^{-1}$. The nuclear magnetic resonance spectrum was in accord with the assigned structure. A toluene solution of the product spotted on an acidic clay or a phenolic resin developed a cyan-colored image.

EXAMPLE 4

A mixture of 15.6 g of 2-(2-methyl-4-diethylaminophenyl)carbonylbenzoic acid, 12.5 g of 1-(2-vinyloxyethyl)-2-methylindole, and 50.0 ml of acetic anhydride was maintained at approximately 70° C. for approximately four hours. The resulting solution was cooled to ambient temperature and slowly poured into a mixture of toluene and 5 percent aqueous ammonium hydroxide. The toluene layer was separated, washed successively once each with water and saturated sodium chloride solution and evaporated to dryness. The residue that remained was heated in a 1:1 mixture of isopropyl alcohol:hexane. The liquid was decanted from a gummy residue. The residue was dissolved in 100.0 ml of acetone and the resulting solution was added dropwise to 1500.0 ml of 2 percent aqueous ammonium hydroxide. The solid which precipitated was collected by filtration, washed with water and dried to obtain 18.86 g of 3-[1-(2-vinyloxyethyl)-2-methylindol-3-yl]-3-(2-methyl-4-diethylaminophenyl)phthalide (Formula I: $R^1$=$CH_2$=$CHOC_2H_4$; $R^1$=$R^2$=$CH_3$; $R^3$=$R^4$=$C_2H_5$; X=Y=H), a tan-colored solid which melted over the range 135°-141° C. Significant infrared maxima appeared at 1760 (C=O;s) and 1120 (C—O;s)cm A toluene solution of the product spotted on an acid clay or a phenolic resin coated paper developed a cyan-colored image.

EXAMPLE 5

A mixture of 10.12 g of 2-[1-(2-methoxyethyl)-2-methylindol-3-yl]carbonylbenzoic acid, 3-methyl-N,N-methylaniline and 80.0 ml of acetic anhydride was maintained at approximately 85° C. overnight. After cooling to ambient temperature the solution was poured slowly into ice water. The solids which precipitated were collected by filtration, washed with water and dried to obtain 12.06 g of dark blue solid. Two grams of the solid was dissolved in a ethyl acetate:toluene (1:3) solution and eluted through a silica gel packed chromatography column using ethyl acetate:toluene (1:3). Fourteen fractions each containing approximately 15 ml were collected. Fractions 1, 2, and 9 through 14 were discarded. The remaining fractions 3 and 4 were combined as were 5 and 6 and 7 and 8. Each of the three combinations were evaporated to dryness. The residue was washed onto a filter with hexane and dried. The three combined fractions were combined to obtain 0.2 g of 3-[1-(2-methoxyethyl)-2-methylindol-3-yl]-3-(2-methyl-4-dimethylaminophenyl)phthalide (Formula I: $R=CH_3OC_2H_4$; $R^1=R^2=R^3=R^4=CH_3$; $X=Y=H$), a tan solid which melted at 205°–207° C. Significant infrared maxima appeared at 1770 ($C=O;s$) and 1125 ($C-O;s$)cm$^{-1}$. A toluene solution of the product spotted on an acidic clay or a phenolic resin coated paper developed a cyan-colored image.

EXAMPLE 6

A mixture of 14.5 g of 2-(2-methyl-4-dimethylaminophenyl)carbonylbenzoic acid, 11.5 g of 1-(2-ethoxyethyl)-2-methylindole and 40.0 ml acetic anhydride was maintained at approximately 70° C. for approximtely four hours. The resulting solution was cooled to ambient temperature and slowly poured into a mixture of toluene and 5 percent aqueous ammonium hydroxide. The toluene layer was separated, washed with water and then with saturated sodium chloride solution. The toluene solution was evaporated to dryness. The residue which remained was recrystallized twice from a mixture of hexane and isopropyl alcohol to obtain 8.9 g of 3-[1-(2-ethxxyethyl)-2-methylindol-3-yl]- 3-(2-methyl-4-dimethylaminophenyl)phthalide (Formula I: $R=C_2H_5OC_2H_4$; $R^1=R^2=R^3=R^4=CH_3$; $X=Y=H$), a white-colored solid which melted at 170.5° to 171° C. Significant infrared maxima appeared at 1750 ($C=O;s$) and 1123 ($C-O;s$)cm$^{-1}$. A toluene solution of the product spotted on an acid clay or a phenolic resin coated paper developed a cyan-colored image.

EXAMPLE 7

A mixture of 14.0 g of 2-(2-methyl-4-diethylaminophenyl)carbonylbenzoic acid, 10.0 g of 1-(2-phenoxyethyl)-2-methylindole and 500.0 ml of acetic anhydride was maintained at approximately 70° C. for approximately four hours. The reaction solution was cooled to ambient temperature and 25.0 ml of isopropyl alcohol was added. The resulting solution was poured slowly into a mixture of 500.0 ml of toluene and 50.0 ml of 5 percent aqueous ammonium hydroxide. The toluene layer was separated, washed with water and then with saturated aqueous sodium chloride solution. The toluene layer was evaporated to dryness. The residue was recrystallized in 150.0 ml of isopropyl alcohol and dried to obtain 20.2 g of 3-[1-(2-phenoxyethyl)-2-methylindol-3-yl]-3-(2-methyl-4-diethylaminophenyl)phthalide (Formula I: $R=C_6H_5OC_2H_4$; $R^1=R^2=CH_3$; $R^3=R^4=C_2H_5$; $X=Y=H$), a white-colored solid which melted at 182°–183° C. Significant infrared maxima appeared at 1750 ($C=O;s$) and 1130 ($C-O;s$)cm$^{-1}$. The nuclear magnetic resonance spectrum was in accord with the assigned structure. A toluene solution of the product spotted on an acidic clay or a phenolic resin coated paper developed a cyan-colored image.

EXAMPLE 8

A. A mixture of 40.0 g of trimellitic anhydride, 60.0 g of 1-(2-methoxyethyl)-2-methylindole and 100.0 ml of glacial acetic acid was heated to approximately 100° C. for approximately one hour and subsequently at approximately 70° C. for approximately four hours. The resulting mixture was cooled to ambient temperature and the solid was collected by filtration. The solid was slurried in 300.0 ml of isopropyl alcohol, collected by filtration, washed twice each time with 50.0 ml of isopropyl alcohol and dried to obtain 33.4 g of 2-[1-(2-methoxyethyl)-2-methylindol-3-yl]-4/5-carboxybenzoic acid, (Formula V: $R=CH_3OC_2H_4$; $R^1=CH_3$; $X=COOH$; $Y=H$), a pale pink-colored solid which melted at 181°–185° C. A significant infrared maximum appeared at 1735 ($C=O;s$)cm$^{-1}$.

B. A mixture of 2-[1-(2-methoxyethyl)-2-methylindol-3-yl) carbonyl-4/5-carboxybenzoic acid from part A directly above, 6.5 g of 3-methyl-N,N-diethylaniline, and 50.0 ml of acetic anhydride was maintained at approximately 70° C. for approximately seventeen hours. After cooling to ambient temperature, 50.0 ml of isopropyl alcohol was added to the reaction mixture and the resulting solution was poured slowly into one liter of 2 percent aqueous sodium chloride solution. The tar-like product which formed was extracted into toluene. The toluene layer was separated, washed with water and then with saturated aqueous sodium chloride solution and evaporated to dryness to obtain 19.0 g of solid which was predominantly 3-[1-(2-methoxyethyl)-2-methylindol-3-yl]-3-(2-methyl-4-N,N-diethylaminophenyl)-5/6-carboxyphthalide (Formula I: $R=CH_3OC_2H_4$; $R^1=R^2=CH_3$; $R^3=R^4=C_2H_5$; $X=COOH$; $Y=H$), a tar-like solid.

C. The 19.0 g of product obtained in part A above was dissolved in 80.0 ml of N,N-dimethylformamide, 11.0 g potassium carbonate was added and the mixture was heated to approximately 40° C. Slowly, 11.0 g of diethyl sulfate was added and the reaction mixture was maintained at approximately 50° C. for approximately ninety minutes. After cooling to ambient temperature, the reaction mixture was filtered to remove a small amount of insolubles which was washed on the filter with 20.0 ml of N,N-dimethylformamide. The combined filtrate and wash was poured slowly into a mixture of 400.0 ml of toluene and 400.0 ml of water. The toluene layer was separated, washed with water and then with saturated aqueous sodium chloride solution and evaporated to dryness. The residue was recrystallized from a mixture of hexane:isopropyl alcohol and the solid collected by filtration. The resulting solid was dissolved in toluene:ethyl acetate (3:1) and separated into various components by subjecting the solution to column chromatography using silica gel as the substrate, eluting with toluene:ethyl acetate (3:1). The fraction containing predominately the desired product was evaporated to dryness. The resulting solid was recrystallized from a mixture of hexane and isopropyl alcohol, collected by filtration and dried to obtain 6.9 g of 3-[1-(2-methoxyethyl)-2-methylindol-3-yl-3-(2-methyl-4-dimethylaminophenyl)- 5/6-ethoxycarbonylphthalide (Formula I: $R=CH_3OC_2H_4$; $R^1=R^2=CH_3$; $R^3=R^4=C_2H_5$; $X=COOC_2H_5$; $Y=H$), a white solid which melted at 151°–153° C. Significant maxima appeared in the infrared at 1765 ($C=O;s$) and 1135 ($C-O;s$)cm$^{-1}$. An acetone solution of the product spotted on an acidic clay or a phenolic resin coated paper developed a cyan-colored image.

EXAMPLE 9

A. Following the procedure described in Example 8, part B above, 25.0 g of 4-nitrophthalic anhydride was interacted with 40.0 g of 1-(2-methoxyethyl)-2-methylindole in 100.0 ml of glacial acetic acid at approximately 110° C. for approximately one hour and at approximately 70° C. for approximately sixteen hours to obtain 38.0 g of 2-[1-(2-methoxyethyl)-2-methylindol-3-yl]carbonyl-4/5-nitrobenzoic acid, (Formula V: $R=CH_3OC_2H_4$; $R^1=CH_3$; $X=NO_2$; $Y=H$), a yellow solid which melted over the range of 150°–155° C. A significant infrared maximum appeared at 1730 $(C=O;s)cm^{-1}$.

B. Proceeding in a manner similar to that described in Example 5, 19.0 g of 2-[1-(2-methoxyethyl)-2-methylindol-3-yl]-carbonyl-4/5-nitrobenzoic acid was interacted with 11.0 g of 3-methyl-N,N-diethylaniline in 70.0 ml of acetic anhydride at approximately 70° C. for approximately eighteen hours to obtain after purification by column chromatography 13.58 g of 3-[1-(2-methoxyethyl)-2-methylindol-3-yl]-3-(2-methyl-4-diethylaminophenyl)-5/6-nitrophthalide, (Formula I: $R=CH_3OC_2H_4$; $R^1=R^2=CH_3$; $R^3=R^4=C_2H_5$; $X=NO_2$; $Y=H$), a yellow solid which melted at 146°–148° C. Significant infrared maxima appeared at 1775 $(C=O;s)$ and 1135 $(C-O;s)cm^{-1}$. An acetone solution of the product spotted on an acidic clay or a phenolic resin developed a cyan-colored image.

EXAMPLE 10

A. Proceeding in a manner similar to that described in part A of Example 8 above, 30.0 g of tetrachlorophthalic anhydride was interacted with 40.0 g of 1-(2-methoxyethyl)-2-methylindole in 75.0 ml of glacial acetic acid at approximately 110° C. for approximately one hour to obtain 55.83 g of 2-[1-(2-methoxyethyl)-2-methylindol-3-yl]carbonyl-3,4,5,6-tetrachlorobenzoic acid, (Formula V: $R=CH_3OC_2H_4$; $R^1=CH_3$; $X=Cl_4$; $Y=H$), a pale yellow solid which melted at 182°–184° C. A significant infrared maximum appeared at 1750 $(C=O;s)$.

B. In a manner similar to that described in part B of Example 8 above 24.0 g of 2-[1-(2-methoxyethyl)-2-methylindol-3-yl]carbonyl-3,4,5,6-tetrachlorobenzoic acid was interacted with 11.0 g 3-methyl-N,N-diethylaniline in 70.0 ml acetic anhydride at approximately 70° C. for approximately four hours to obtain after purification by column chromatography 0.98 g of 3-[1-(2-methoxyethyl)-2-methylindol-3-yl]-3-(2-methyl-4-dimethylaminophenyl)-4,5,6,7-tetrachlorophthalide, (Formula I: $R=CH_3 OC_2H_4$; $R^1=R^2=R^3=R^4=CH_3$; $X=Cl_4$; $Y=H$), a tan-colored solid which melted at 119°–123° C. Significant infrared maxima appeared at 1768 $(C=O;s)$ and 1160 $(C-O;s)cm^{-1}$. An acetone solution of the product spotted on an acidic clay or a phenolic resin coated paper developed a cyan-colored image.

EXAMPLE 11

In a manner similar to that described in part B of Example 8 above 20.0 g of 2-(2-methyl-4-diethylaminophenyl)carbonylbenzoic acid was interacted with 11.0 g of 1-(2-methoxyethyl)indole in 50.0 ml of acetic anhydride at approximately 70° C. for approximately eighteen hours to obtain after recrystallization from a mixture of isopropyl alcohol and hexane, 11.24 g of 3-[1-(2-methoxyethyl)indol-3-yl]-3-(2-methyl-4-dimethylaminophenyl)phthalide, [Formula I: $R=CH_3OC_2H_4$; $R^1=X=Y=H$; $R^2=CH_3$; $R^3=R^4=C_2H_5$), a white solid which melted at 144°–146° C. Significant infrared maxima appeared at 1760 $(C=O;s)$ and 1121 $(C-O;s)cm^{-1}$. An acetone solution of the product spotted on an acidic clay or a phenolic resin coated paper developed a blue-colored image.

EXAMPLE 12

A. A mixture of 25.0 g of pyridine-2,3-dicarboxylic anhydride, 45.0 g of 1-(2-ethoxyethyl)-2-methylindole and 150.0 ml of glacial acetic acid was heated at a temperature in the range of 70° to 75° C. for approximately eight hours. The resulting reaction mixture was cooled to ambient temperatures. The solid which formed was collected by filtration, washed three times each with 50.0 ml of methyl alcohol and dried to obtain 45.2 g of a mixture of 2-[1-(2-methoxyethyl)-2-methylindol-3-yl]carbonylpyridine 3-carboxylic acid and 3-[1-(2-ethoxyethyl)-2-methylindol-3-yl]carbonylpyridine-2-carboxylic acid (Formulas VIII and IV: $R=C_2H_5OC_2H_4$; $R^1=CH_3$), a pale pink solid which melted at 183°–185° C. Significant infrared maxima appeared at 1725 $(C=O;s)$ and 1240 $(C-O;s)cm^{-1}$. The nuclear magnetic resonance spectrum was in accord with the assigned structure.

B. A mixture of 11.3 g of the product obtained in part A directly above, 6.5 g of 3-methyl-N,N-diethylaniline and 40.0 ml of acetic anhydride was heated at approximately 70° C. for approximately six hours. After cooling to ambient temperature, the reaction mixture was poured slowly into a mixture of 300.0 ml of toluene and 300.0 ml of five percent aqueous ammonium hydroxide. The toluene layer was separated, washed first with water, and then with saturated aqueous sodium chloride solution and finally evaporated to dryness. The resulting residue was recrystallized from a hot mixture of isopropyl alcohol and hexane, the solid was collected by filtration from the hot mixture and dried to obtain 1.6 g of the starting material from part A. The resulting filtrate was evaporated to dryness. The residue was recrystallized from isopropyl alcohol, the solid collected by filtration and dried to obtain 2.8 g of a mixture of 7-[1-(2-ethoxyethyl)-2-methylindol-3-yl]-7-(2-methyl-4-diethylamino phenyl)-furo[3,4-b]pyridine-5(7H)-one and 5-[1-(2-ethoxyethyl)-2-methylindol-3-yl]-5-(2-methyl-4-diethylaminophenyl)furo(3,4-b)-pyridine-7(5H)-one (Formulas II and III: $R=C_2H_5OC_2H_4$; $R^1=R^2=CH_3$; $R^3=R^4=C_2H_5$; $Y=H$), a pale brown solid which melted at 132°–135° C. Significant infrared maxima appeared at 1770 $(C=O;s)$ and 1140 $(C-O;s)cm^{-1}$. The nuclear magnetic resonance spectrum was concordant with the assigned structure. A toluene solution of the product spotted on an acidic clay or a phenolic resin coated paper developed a turquoise-colored image.

EXAMPLE 13

A mixture of 19.0 g of 2-[1-(2-methoxyethyl)-2-methylindol-3-yl]carbonyl-4/5-chlorobenzoic acid, 10.0 g of 3-methyl-N,N-diethylaniline and 40.0 ml of acetic anhydride was maintained at approximately 70° C. for approximately 18 hours. After cooling to ambient temperature, the reaction mixture was poured slowly into a mixture of 350.0 ml toluene and 350.0 ml 10 percent aqueous ammonium hydroxide. The toluene layer was separated, washed with water and then washed with saturated aqueous sodium chloride solution and evaporated to dryness. The resulting residue was triturated three times each with 100.0 ml of hexane. The resulting tar-like solid was then dissolved in a 3:1 mixture of toluene:ethyl acetate and the solution was passed through a chromatography column packed with silica gel using toluene:ethyl acetate to elute the product. The collected fractions containing predominantly the desired product were combined, evaporated to dryness and the resulting residue was triturated with hexane to obtain after filtration and drying 2.92 g of 3-[1-(2-methoxyethyl)-2-methylindol-3-yl]-3-(2-methyl-4-diethylaminophenyl)-5/6-chlorophthalide (Formula I: $R=CH_3OC_2H_2$; $R^1=R^2=CH_3$; $R^3=R^4=C_2H_5$; $X=Cl$; $Y=H$), a pale yellow solid which melted at 78° to 81° C. Significant infrared maxima appeared at 1765 ($C=O;s$) and 1128 ($C-O;s$)cm$^{-1}$. The nuclear magnetic resonance spectrum was in accord with the assigned structure. An acetone solution of the product spotted on an acidic clay or a phenolic resin coated paper developed a cyan-colored image.

EXAMPLE 14

A. Proceeding in a manner similar to that described in part A of Example 12, above, 25.0 g of pyridine-2,3-dicarboxylic anhydride was interacted with 45.0 g of 1-(2-methoxyethyl)-2-methylindole in 70.0 ml of glacial acetic acid at approximately 75° C. for approximately six hours to obtain 45.1 g of a mixture of 2-[1-(2-methoxyethyl)-2-methylindol-3-yl]carbonylpyridine-3-carboxylic acid and 3-[1-(2-methoxyethyl)-2-methylindol-3-yl)]carbonylpyridine -2-carboxylic acid (Formulas VIII and IX: $R=CH_3OC_2H_4$; $R^1=CH_3$), a pale purple-colored solid which melted over the range 178°–183° C. Significant infrared maxima appeared at 1730 ($C=O;s$) and 1240 ($C-O;s$) cm$^{-1}$.

B. Following the procedure described in part B of Example 12 above, 17.0 g of the product obtained in part A directly above was interacted with 8.0 g of 3-methyl-N,N-dimethylaniline in 50.0 ml of acetic anhydride at approximately 70° C. for approximately eighteen hours. The residue from the toluene layer was dissolved in a mixture of toluene:ethyl acetate (3:1) and the solution passed through s chromatography column packed with silica gel. Several fractions containing the desired product were combined and partially concentrated. The solid which formed was collected by filtration, and dried to obtain 2.63 g of a mixture of 7-[1-(2-methoxyethyl)-2-methylindol-3-yl]-7-(2-methyl-4-dimethylamino-phenyl)furo[3,4-b]pyridine-5(7H)-one and 5-[1-(2-methoxyethyl)-2-methylindol-3-yl]-5-(2-methyl-4-dimethylaminophenyl)furo[3,4-b]-pyridine-7(5H)one, (Formulas II and III: $R=CH_3OC_2H_4$; $R^1=R^2=R^3=R^4=CH_3$; $Y=H$), a pale yellow-colored solid which melted at 214°–215° C. Significant infrared maxima appeared at 1760 ($C=O;s$) and 1140 ($C-O;s$)cm$^{-1}$. A toluene solution of the product spotted on an acidic clay or a phenolic resin coated paper developed a cyan-colored image.

EXAMPLE 15

A mixture of 11.3 g of a mixture of 2-[1-(2-methoxyethyl)-2-methylindol-3-yl]carboxylpyridine-3-carboxylic acid and 3-[1-(2-methoxyethyl)-2-methylindol-3-yl]carbonylpyridine-2-carboxylic acid, 6.5 g of 3-methyl-N,N-diethylaniline and 40.0 ml acetic anhydride was maintained at approximately 70° C. for approximately six hours. After cooling to ambient temperature the reaction mixture was poured slowly into a mixture of 300.0 ml of toluene and 300.0 ml of 5 percent aqueous ammonium hydroxide. The toluene layer was separated, washed with water and subsequently with a saturated aqueous sodium chloride solution and finally evaporated to dryness. The residue was heated in a mixture of isopropyl alcohol and hexane. The solid which did not dissolve was filtered from the hot liquid and upon drying there was obtained 1.6 g of unreacted pyridine carboxylic acids. The filtrate was evaporated to dryness and the residue was crystallized from isopropyl alcohol, collected by fitration and dried to obtain 2.8 g of a mixture of 7-[1-(2-methoxyethyl)-2-methylindol-3-yl]-7-(2-methyl-4-diethyl-aminophenyl)-furo[3,4-b]pyridine-5(7H)-one and 5-[1-(2-methoxy-ethyl)-2-methylindol-3-yl]-5-(2-methyl-4-diethylaminophenyl)-furo[3,4-b]pyridine-7(5H)-one (Formulas II and III: $R=CH_3OC_2H_4$; $R^1=R^2=CH_3$; $R^3=R^4=C_2H_5$; $Y=H$), a tan colored solid which melted at 132°–135° C. Significant infrared maxima appeared at 1770 ($C=O;s$) and 1140 ($C-O;s$) cm$^{-1}$. An acetone solution of the product spotted on an acidic clay or a phenolic resin coated paper developed a turquoise-colored image.

Proceeding in a manner similar to that described in Example 1 above, the appropriate substituted benzoic acid described in the second column of Part 1 of table A hereinbelow was interacted with the substituted indole or the substituted aniline described in the third column of Part 1 in the amount of acetic anhydride given in the fourth column of Part 1 at a temperature of the reaction mixture given in the fifth column of Part 1 for the period of time indicated in the sixth column of Part 1. The product obtained is given in the second column of Part 2 of Table A having the structural formula referred to in the third column of Part 2 with its physical appearance described in the fourth column of Part 2. Its melting point is shown in the fifth column of Part 2, and significant infrared maximum is indicated in the sixth column of Part 2. The color produced when a toluene solution of the product was spotted on an acidic clay or a phenolic resin coated paper is described in the seventh column of Part 2.

TABLE A

PART I

| Example Number | Starting Benzoic Acid | Indole or Aniline | Acetic Anhydride | Temp. | Reaction Time |
|---|---|---|---|---|---|
| 16 | 20.0 g 2-(4-Dimethylaminophenyl)carbonylbenzoic Acid | 16.6 g 1-(2-Methoxyethyl)-2-methylindole | 50.0 ml | 75° C. | 18 hours |
| 17 | 19.0 g 2-[1-Methoxyethyl)-2-methylindol-3-yl]carbonyl-4/5 chlorobenzoic acid | 12.0 g 3-Ethoxy-N,N—diethylaniline | 50.5 ml | 70° C. | 18 hours |
| 18 | 10.1 g 2-[1-(2-Methoxyethyl)-2-methylindol-3-yl]carbonyl-benzoic acid | 6.4 g 3-Ethoxy-N,N—diethylaniline | 80.0 ml | 80° C. | 8 hours |
| 19 | 10.0 g 2-[1-(2-Phenoxyethyl)-2- | 8.0 g 3-Ethoxy-N,N—diethylaniline | 30.0 ml | Reflux | 1 hour |

TABLE A-continued

| | | | | | | |
|---|---|---|---|---|---|---|
| | | methylindol-3-yl]carbonyl-benzoic acid | | | 80–85° C. | 1 hour |
| 20 | 17.0 g | 2-[1-(2-Methoxyethyl)-2-methylindol-3-yl]carbonyl-benzoic acid | 11.0 g | 3-Acetamido-N,N—diethylaniline | 120.0 ml | 70° C. | 18 hours |
| 21 | 17.0 g | 2-[1-(2-Methoxyethyl)-2-methylindol-3-yl]carbonyl-benzoic acid | 17.0 g | 3-Methyl-N—ethyl-N—octylaniline | 100.0 ml | 70° C. | 18 hours |
| 22 | 17.0 g | 2-[1-(2-Methoxyethyl)-2-methylindol-3-yl]carbonyl-benzoic acid | 12.0 g | N,N,N,N—Tetramethyl meta-phenylene diamine | 100.0 ml | 70° C. | 18 hours |
| 23 | 15.0 g | 2-(2-Methyl-4-diethylamino-phenyl)carbonylbenzoic acid | 12.1 g | 1-(2-Butoxyethyl)2-methylindole | 75.0 ml | 75° C. | 16 hours |
| 24 | 3.7 g | 2-(2-Methyl-4-diethylamino-phenyl)carbonylbenzoic acid | 2.5 g | 1-(2-Methoxyethyl)2,5-dimethylindole | 50.0 ml | 75° C. | 16 hours |
| 25 | 11.0 g | 2-(2-Methyl-4-diethylamino phenyl)carbonylbenzoic acid | 8.0 g | 1-(2-Methoxyethyl)2-methyl-5-methoxyindole | 75.0 ml | 75° C. | 18 hours |

PART II

| Example Number | Product Obtained | Product Formula | Physical Appearance | Melting Point | Significant Infrared | Produced Image Color |
|---|---|---|---|---|---|---|
| 16 | 21.4 g 3-(4-Diethylaminophenyl)-3-[1-(2-methoxyethyl)-indol-3-yl]phthalide | I: $R=CH_3OC_2H_4$; $R^1=R^2=X^3=Y=H$; $R^3=R^4=CH_3$ | Pale red powder | 79–85° C. | 1760 cm$^{-1}$ (C=O;s) | Blue |
| 17 | 6.8 g 3-(2-Ethoxy-4-diethylamino-phenyl)-3-[1-(2-methoxy-ethyl)-2-methylindol-3-yl]-5/6-chlorophthalide | $R=CH_3OC_2H_4$; $R^1=CH_3$; $R^2=C_2H_5O$; $R^3=R^4=C_2H_5$; $X=Cl$; $Y=H$ | White powder | 172–174° C. | 1765 cm$^{-1}$ (C=O;s) | Purple |
| 18 | 13.3 g 3-(2-Ethoxy-4-diethylamino-phenyl)-3-[1-(2-methoxyethyl)2-methylindol-3-yl]phthalide | I: $R=CH_3OC_2H_4$; $R^1=CH_3$; $R^2=C_2H_5O$; $R^3=R^4=C_2H_5$; $X=Y=H$ | Pale blue powder | 169–172° C. | 1750 cm$^{-1}$ (C=O;s) | Blue |
| 19 | 12.6 g 3-(2-Ethoxy-4-diethylamino-phenyl)-3-[1-(2-phenoxyethyl)-2-methylindol-3-yl]phthalide | I: $R=C_6H_5OC_2H_5$; $R^1=CH_3$ $R^2=C_2H_5O$; $R^3=R^4=C_2H_5$; $X=Y=H$ | Pale tan powder | 132–135° C. | 1746 cm$^{-1}$ (C=O;s) | Blue |
| 20 | 14.1 g 3-(2-Acetamido-4-diethylamino-phenyl)-3-[1-(2-methoxyethyl)-2-methylindol-3-yl]phthalide | I: $R=CH_3OC_2H_4$; $R^1=CH_3$; $R^2=CH_3COHN$; $R^3=R^4=C_2H_5$; $X=Y=H$ | White powder | 185–187° C. | 1770 cm$^{-1}$ (C=O;s) | Blue |
| 21 | 10.2 g 3-(2-Methyl-4-N—ethyl-N—octyl-aminophenyl)-3-[1-(2-methoxy-ethyl)-2-methylindol-3-yl]phthalide | I: $R=CH_3OC_2H_4$; $R^1=R^2=CH_3$; $R^3=C_2H_5$; $R^4=C_8H_{17}$; $X=Y=H$ | White powder | 87–93° C. | 1755 cm$^{-1}$ (C=O;s) | Cyan |
| 22 | 7.4 g 3-[2,4-bis(dimethylamino)-phenyl]-3-[1-(2-methoxyethyl)-2-methylindol-3-yl]phthalide | I: $R=CH_3OC_2H_4$; $R^1=R^3=R^4=CH_3$; $R^2=(CH_3)_2N$; $X=Y=H$ | White powder | 159–160° C. | 1758 cm$^{-1}$ (C=O;s) | Violet |
| 23 | 10.7 g 3-(2-Methyl-4-diethylamino-phenyl)-3-[1-(2-butoxyethyl)2-methylindol-3-yl]phthalide | I: $R=C_4H_9OC_2H_4$; $R^1=R^2=CH_3$; $R^3=R^4=C_2H_5$; $X=Y=H$ | Pale tan powder | 125–130° C. | 1760 cm$^{-1}$ (C=O;s) | Cyan |
| 24 | 3.4 g 3-(2-Methyl-4-diethylamino-phenyl)-3-[1-(2-methoxyethyl)2,5-dimethylindol-3-yl]phthalide | I: $R=CH_3OC_2H_4$; $R^1=R^2=Y=CH_3$; $R^3=R^4=C_2H_5$; $X=H$ | Cream powder | 124–127° C. | 1760 cm$^{-1}$ (C=O;s) | Cyan |
| 25 | 14.7 g 3-(2-Methyl-4-diethylamino-phenyl)-3-[1-(2-methoxyethyl)-2-methyl-5-methoxyindol-3-yl]phthalide | I: $R=CH_3OC_2H_4$; $R^1=R^2=CH_3$; $R^3=R^4=C_2H_5$; $X=H$; $Y=CH_3O$ | Pale tan powder | 121–124° C. | 1760 cm$^{-1}$ (C=O;s) | Cyan |

Proceeding in a manner similar to that described in Example 2 above, the appropriate substituted benzoic acid described in the second column of Part 1 of table B hereinbelow was interacted with the substituted indole or the substituted aniline described in the third column of Part 1 in the amount of acetic anhydride given in the fourth column of Part 1 at a temperature of the reaction mixture given in the fifth column of Part 1 for the period of time indicated in the sixth column of Part 1. The product obtained is given in the second column of Part 2 of Table B having the structural formula referred to in the third cllumn of Part 2 with its physical appearance described in the fourth column of Part 2. Its melting point is shown in the fifth column of Part 2, and significant infrared maximum is indicated in the sixth column of Part 2. The color produced when a toluene solution of the product was spotted on an acidic clay or a phenolic resin coated paper is described in the seventh column of Part 2.

TABLE B

PART I

| Example Number | Starting Benzoic Acid | Indole or Aniline | Acetic Anhydride | Temp. | Reaction Time |
|---|---|---|---|---|---|
| 26 | 17.0 g 2-[(2-Methoxyethyl)-2- | 16.0 g 3-Methyl-N—(2-hydroxyethyl)-N—ethylaniline | 80.0 ml | 70° C. | 17 hours |

TABLE B-continued

| | | | | | | | |
|---|---|---|---|---|---|---|---|
| | | methylindol-3-yl]carbonyl-benzoic acid | | | | | |
| 27 | 20.7 g | 2-[4-Dimethylaminophenyl)-carbonyl-5-dimethylamino-benzoic acid | 14.2 g | 1-(2-Methoxyethyl)-2-methylindole | 50.0 ml | 75° C. | 18 hours |
| 28 | 17.0 g | 2-[1-(2-Methoxyethyl)-2-methylindol-3-yl]carbonyl-benzoic acid | 14.0 g | 3-Methyl-piperidinylbenzene | 100.0 ml | 70° C. | 18 hours |
| 29 | 17.0 g | 2-[1-(2-Methoxyethyl)-2-methylindol-3-yl]carbonyl-benzoic acid | 12.0 g | 3-Methyl-N—methyl-N—benzylaniline | 100.0 ml | 70° C. | 6 hours |
| 30 | 17.0 g | 2-[1-(2-Methoxyethyl)-2-methylindol-3-yl]carbonyl-benzoic acid | 10.0 g | 3-Ethyl-N,N—diethylaniline | 50.0 ml | 70° C. | 5 hours |

PART II

| Example Number | Product Obtained | Product Formula | Physical Appearance | Melting Point | Significant Infrared | Produced Image Color |
|---|---|---|---|---|---|---|
| 26 | 1.9 g 3-[2-Methyl-4-N—(2-hydroxyethyl)-N—ethylaminophenyl]-3-[1-(2-methoxyethyl)-2-methylindol-3-yl]phthalide | I: $R=CH_3OC_2H_4$; $R^1=R^2=CH_3$; $R^3=HOC_2H_4$; $R^4=C_2H_5$; $X=Y=H$ | Pale pink powder | 100–104° C. | 1760 cm$^{-1}$ (C=O;s) | Cyan |
| 27 | 12.5 g 3-(4-Dimethylaminophenyl)-3-[1-(2-methoxyethyl)-2-methylindol-3-yl]-6-dimethyl-aminophthalide | I: $R=CH_3OC_2H_4$; $R^1=R^3=R^4=CH_3$; $R^2=Y=H$; $X=(CH_3)_2N$ | Tan powder | 111–115° C. | 1760 cm$^{-1}$ (C=O;s) | Violet |
| 28 | 3.6 g 3-(2-Methyl-4-piperidinyl-phenyl)-3-[1-2-methoxyethyl)-2-methylindol-3-yl]phthalide | I: $R=CH_3OC_2H_4$; $R^1=R^2=CH_3$; $R^3+R^4=C_5H_{10}$; $X=Y=H$ | White powder | 159–161° C. | 1755 cm$^{-1}$ (C=O;s) | Cyan |
| 29 | 1.3 g 3-[2-Methyl-4-(N—methyl-N—benzylamino)phenyl]-3-[1-(2-methoxyethyl)-2-methylindol-3-yl]phthalide | I: $R=CH_3OC_2H_4$; $R^1=R^2=R^3=CH_3$; $R^4=C_6H_5CH_2$; $X=Y=H$ | Pale yellow powder | 120–125° C. | 1760 cm$^{-1}$ (C=O;s) | Cyan |
| 30 | 2.9 g 3-(2-Ethyl-4-diethylamino-phenyl)-3-[1-2-methoxyethyl)-2-methylindol-3-yl]phthalide | I: $R=CH_3OC_2H_4$; $R^1=CH_3$; $R^2=R^3=R^4C_2H_5$; $X=Y=H$ | White powder | 167–169° C. | 1750 cm$^{-1}$ | Cyan |

Proceeding in a manner similar to that described in Example 12B above, the appropriate substituted benzoic acid described in the second column of Part 1 of Table C hereinbelow was interacted with the substituted indole or the substituted aniline described in the third column of Part 1 in the amount of acetic anhydride given in the fourth column of Part 1 at a temperature of the reaction mixture given in the fifth column of Part 1 for the period of time indicated in the sixth column of Part 1. The product obtained is given in the second column of Part 2 of Table C having the structural formula referred to in the third column of Part 2 with its physical appearance described in the fourth column of Part 2. Its melting point is shown in the fifth column of Part 2, and significant infrared maximum is indicated in the sixth column of Part 2. The color produced when a toluene solution of the product was spotted on an acidic clay or a phenolic resin coated paper is described in the seventh column of Part 2.

TABLE C

PART I

| Example Number | Starting Pyridinecarboxylic Acid | | Indole or Aniline | Acetic Anhydride | Temp. | Reaction Time |
|---|---|---|---|---|---|---|
| 31 | 17.0 g | of a mixture of 2/3-[1-(2-methoxyethyl)-2-methylindol-3-yl]carbonyl-3/2-pyridine-carboxylic acid | 10.0 g 3-Ethyl-N,N—diethylaniline | 50.0 ml | 70° C. | 6 hours |
| 32 | 17.0 g | of a mixture of 2/3-[1-(2-methoxyethyl)-2-methylindol-3-yl]-3/2-pyridinecarboxylic acid | 12.0 g 3-Methyl-N—methyl-N—benzylaniline | 100.0 ml | 70° C. | 6 hours |
| 33 | 17.0 g | a mixture of 2/3-[1-(2-ethoxyethyl)-2-methylindol-3-yl]-3/2-pyridinecarboxylic acid | 8.0 g 2-Ethoxy-N,N—diethylaniline | 40.0 ml | 70° C. | 6 hours |
| 34 | 18.0 g | of a mixture of 2/3-[1-(2-methoxyethyl)-2-methylindol-3-yl]3/2-pyridinecarboxylic acid | 11.4 g 2-Ethoxy-N,N—diethylaniline | 60.0 ml | 70° C. | 7 hours |

PART II

| Example Number | Product Obtained | Product Formula | Physical Appearance | Melting Point | Significant Infrared | Produced Image Color |
|---|---|---|---|---|---|---|
| 31 | 1.8 g of a mixture of 7/5-(2-Ethyl-4-diethylaminophenyl)-7/5-[1-(2-methoxyethyl)-2-methyl-indol-3-yl]furo[3,4b]pyridine-5/7-(7H/5H)—one | II & III: $R=CH_3OC_2H_4$; $R^1=CH_3$; $R^2=R^3=R^4=C_2H_5$; $Y=H$ | White powder | 196–197° C. | 1770 cm$^{-1}$ | Cyan |
| 32 | 0.26 g of a mixture of 7/5-[2- | II & III: | Yellow powder | 79–83° C. | 1765 cm$^{-1}$ | Cyan |

TABLE C-continued

| | | | | | | | |
|---|---|---|---|---|---|---|---|
| | | methyl-4-(N—methyl-N—benzyl-amino)phenyl]-7/5-[1-(2-methoxyethyl)-2-methylindol-3-yl]furo[3,4b]-pyridine-5/7-(7H/5H)—one | $R=CH_3OC_2H_4$; $R^1=R^2=R^3=CH_3$; $R^4=C_6H_5CH_2$; $Y=H$ | | | (C=O;s) | |
| 33 | 16.7 g | of a mixture of 7/5-(2-ethoxy-4-diethylaminophenyl)-7/5-[1-(2-ethoxyethyl)-2-methylindol-3-yl]furo[3,4b]-pyridine-5/7-(7H/5H)—one | II & II: $R=C_2H_5OC_2H_4$; $R^1=CH_3$; $R^2=C_2H_5O$; $R^3=R^4=C_2H_5$; $Y=H$ | White powder | 109–111° C. | 1760 cm$^{-1}$ (C=O;s) | Blue |
| 34 | 14.2 g | of a mixture of 7/5-(2-ethoxy-4-diethylaminophenyl)-7/5-[1-(2-methoxyethyl)-2-methyl-indol-3-yl]furo[3,4b]-pyridine-5/7(7H/5H)—one | II & III: $R=CH_3OC_2H_4$; $R^1=CH_3$; $R^2=C_2H_5O$; $R^3=R^4=C_2H_5$; $Y=H$ | White powder | 127–130° C. | 1760 cm$^{-1}$ (C=O;s) | Cyan |

It is contemplated that by following the procedure described in the foregoing examples but employing the appropriate 2-(1-R-2-$R^1$-5/6-Y-indol-3-yl)carbonyl-X-benzoic acid of Formula V with the appropriate 3-$R^2$-N-$R^3$-N-$R^4$-aniline of Formula VII or the appropriate 2-(2-$R^2$-4-N-$R^3$-N-$R^4$-aminophenyl)carbonyl-X-benzoic acid of Formula VI with the appropriate 1-R-2-$R^1$-5/6-Y-indole of Formula IV, there will be obtained a 3-(2-$R^2$-4-N-$R^3$-N-$R^4$-aminophenyl)-3-(1-R-2-$R^1$-5/6-Y-indol-3-yl)-X-phthalide of Formula I, presented in Examples 35 to 50, presented in Table D hereinbelow.

VIII and IX with the appropriate 3-$R^2$-N-$R^3$-N-$R^4$-aniline of Formula VII, there will be obtained a mixture of 7/5-(2-$R^2$-4-N-$R^3$-N-$R^4$-aminophenyl)-7/5-(1-R-2-$R^1$-5/6-Y-indol-3-yl)furo[3,4b]-pyridine-5/7(7H/5H)-ones of Formulas II and III presented in Examples 51 to 66, presented in Table E hereinbelow.

TABLE E

| Example No. | R | $R^1$ | $R^2$ | $R^3$ | $R^4$ | Y |
|---|---|---|---|---|---|---|
| 51 | $CH_3OC_3H_6$— | $C_6H_5$ | $C_4H_9$ | $C_6H_5CH_2$ | $C_6H_5CH_2$ | 5-$OC_2H_5$ |
| 52 | $C_4H_9OC_3H_6$— | $C_4H_9$ | $CF_3$ | $C_3H_7$ | $C_3H_7$ | 6-Cl |
| 53 | $C_6H_5OC_3H_6$— | $C_3H_7$ | $N(C_2H_5)_2$ | $C_4H_9$ | $C_4H_9$ | 5,6-$Cl_2$ |
| 54 | 4-$MeC_6H_4OC_2H_4$— | $C_6H_5$ | $N(C_4H_9)_2$ | $C_2H_5$ | $C_6H_5CH_2$ | 5-$NO_2$ |
| 55 | 2,4-$(CH_3O)_2C_6H_3OC_2H_4$— | $C_6H_5$ | $NHCOCH_3$ | $C_2H_5$ | 4-$CH_3C_6H_5CH_2$ | 5,6-$(CH_3)_2$ |
| 56 | 2-$ClC_6H_4OC_2H_4$— | $C_2H_5$ | $NHCOC_2H_5$ | 4-$ClC_6H_4CH_2$ | $C_3H_7$ | 6-$C_2H_5$ |
| 57 | $C_4H_7OC_3H_6$— | $C_6H_5$ | $C_3H_7$ | 3-$NC_2C_6H_4CH_2$ | $CH_3$ | 5-Br |
| 58 | $C_2H_5OC_3H_6$— | $CH_3$ | $OC_8H_{17}$ | $C_2H_4OC_2H_4OCH_3$ | $CH_3$ | 6-$NO_2$ |
| 59 | $C_3H_7OC_3H_6$— | $C_3H_7$ | $N(C_3H_7)_2$ | $C_4H_9$ | $C_2H_4OC_4H_9$ | 5-$C_3H_7$ |
| 60 | $C_3H_5OC_3H_6$— | $C_4H_9$ | $N(CH_3)_2$ | $C_2H_4OH$ | $C_2H_4OH$ | 5/6-$(CH_3O)_2$ |
| 61 | 4-$NO_2C_6H_4OC_3H_6$— | $C_6H_5$ | $OC_4H_9$ | $C_2H_4OCH_3$ | $C_2H_4OCH_3$ | 6-$C_2H_5O$ |
| 62 | 2,4-$(CH_3)_2C_6H_3OC_2H_4$— | $CH_3$ | $NHCOC_4H_9$ | 2,4-$(CH_3)_2C_6H_3CH_2$ | $CH_3$ | 5-$NO_2$ |
| 63 | $C_6H_{13}OC_3H_6$— | $C_4H_9$ | $CF_3$ | $C_2H_5$ | 2,4-$(Cl)_2C_6H_3CH_2$ | 5,6-$(CH_3)_2$ |
| 64 | 2,4-$(Br)_2C_6H_3OC_2H_4$— | $C_3H_7$ | $NHCOCH_3$ | $C_6H_5CH_2$ | $C_4H_9$ | 6-$C_2H_5$ |
| 65 | 4-$C_2H_5C_6H_4OC_3H_6$— | $C_6H_5$ | $N(C_4H_9)_2$ | $CH_3$ | $C_3H_7$ | 6-Br |
| 66 | 4-$C_4H_9C_6H_4OC_3H_6$— | $CH_3$ | $NHCOC_4H_9$ | $C_4H_9$ | $C_2H_5$ | 5-F |

EXAMPLE 67

The use of the compounds of Formulas I, II, and III described in the foregoing examples, as color-forming components in pressure-sensitive microencapsulated copying systems is illustrated by the incorporation and

TABLE D

| Example No. | R | $R^1$ | $R^2$ | $R^3$ | $R^4$ | X | Y |
|---|---|---|---|---|---|---|---|
| 35 | $CH_3OC_3H_6$— | $C_6H_5$ | $C_4H_9$ | $C_6H_5CH_2$ | $C_6H_5CH_2$ | 6-F | 5-$OC_2H_5$ |
| 36 | $C_4H_9OC_3H_6$— | $C_4H_9$ | $CF_3$ | $C_3H_7$ | $C_3H_7$ | 4,5,6,7-$Br_4$ | 6-Cl |
| 37 | $C_6H_5OC_3H_6$— | $C_3H_7$ | $N(C_2H_5)_2$ | $C_4H_9$ | $C_4H_9$ | 5/6-$COOCH_2C_6H_5$ | 5,6-$Cl_2$ |
| 38 | 4-$MeC_6H_4OC_2H_4$— | $C_6H_5$ | $N(C_4H_9)_2$ | $C_2H_5$ | $C_6H_5CH_2$ | 5/6-$COOC_4H_9$ | 5-$NO_2$ |
| 39 | 2,4-$(CH_3O)_2C_6H_3OC_2H_4$— | $C_6H_5$ | $NHCOCH_3$ | $C_2H_5$ | 4-$CH_3C_6H_5CH_2$ | 5/6-$COOC_{16}H_{33}$ | 5,6-$(CH_3)_2$ |
| 40 | 2-$ClC_6H_4OC_2H_4$— | $C_2H_5$ | $NHCOC_2H_5$ | 4-$ClC_6H_4CH_2$ | $C_3H_7$ | 5/6-$COOCH_2C_6H_4Cl$ | 6-$C_2H_5$ |
| 41 | $C_4H_7OC_3H_6$— | $C_6H_5$ | $C_3H_7$ | 3-$NC_2C_6H_4CH_2$ | $CH_3$ | 5/6-$COOC_{12}H_{26}$ | 5-Br |
| 42 | $C_2H_5OC_3H_6$— | $CH_3$ | $OC_8H_{17}$ | $C_2H_4OC_2H_4OCH_3$ | $CH_3$ | 6-$N(C_4H_4)_2$ | 6-$NO_2$ |
| 43 | $C_3H_7OC_3H_6$— | $C_3H_7$ | $N(C_3H_7)_2$ | $C_4H_9$ | $C_2H_4OC_4H_9$ | 6-$N(C_2H_5)_2$ | 5-$C_3H_7$ |
| 44 | $C_3H_5OC_3H_6$— | $C_4H_9$ | $N(CH_3)_2$ | $C_2H_4OH$ | $C_2H_4OH$ | 5-$N(C_2H_5)_2$ | 5/6-$(CH_3O)_2$ |
| 45 | 4-$NO_2C_6H_4OC_3H_6$— | $C_6H_5$ | $OC_4H_9$ | $C_2H_4OCH_3$ | $C_2H_4OCH_3$ | 5/6-$Cl_2$ | 6-$C_2H_5O$ |
| 46 | 2,4-$(CH_3)_2C_6H_3OC_2H_4$— | $CH_3$ | $NHCOC_4H_9$ | 2,4-$(CH_3)_2C_6H_3CH_2$ | $CH_3$ | 5-I | 5-$NO_2$ |
| 47 | $C_6H_{13}OC_3H_6$— | $C_4H_9$ | $CF_3$ | $C_2H_5$ | 2,4-$(Cl)_2C_6H_3CH_2$ | 6-I | 5,6-$(CH_3)_2$ |
| 48 | 2,4-$(Br)_2C_6H_3OC_2H_4$— | $C_3H_7$ | $NHCOCH_3$ | $C_6H_5CH_2$ | $C_4H_9$ | 4,6-$Cl_2$ | 6-$C_2H_5$ |
| 49 | 4-$C_2H_5C_6H_4OC_3H_6$— | $C_6H_5$ | $N(C_4H_9)_2$ | $CH_3$ | $C_3H_7$ | $N(C_3H_7)_2$ | 6-Br |
| 50 | 4-$C_4H_9C_6H_4OC_3H_6$— | $CH_3$ | $NHCOC_4H_9$ | $C_4H_9$ | $C_2H_5$ | 5/6-$COOC_3H_7$ | 5-F |

It is contemplated that by following the procedure described in the foregoing examples but employing the appropriate mixture of 2/3-(1-R-2-$R^1$-5/6-Y-indol-3-yl)carbonylpyridine-3/2-carboxylic acids of Formulas the testing of the compound of Example 1, 3-[1-(2-methoxyethyl)-2-methylindol-3-yl]-3-(2-methyl-4-diethylaminophenyl)phthalide in a pressure-sensitive marking paper. The test paper was prepared by a procedure similar to that described in U.S. Pat. No. 4,275,905.

A. A mixture of 7.8 g of 10 percent aqueous EMA 31 (ethylene-maleic anhydride copolymer with a molecular weight range of 75,000 to 90,000, supplied by Monsanto Chemical Co.), 14.5 g of 10 percent aqueous EMA 1104 (ethylene-maleic anhydride copolymer with a molecular weight range of 5,000 to 7,000, supplied by Monsanto Chemical Co.), 78.0 ml of distilled water was adjusted to pH 4.0 with the addition of 25 percent aqueous sodium hydroxide. A solution was prepared by dissolving 1.2 g of 3-[1-(2-methoxyethyl)-2-methylindol-3-yl]-3-(2-methyl-4-diethylaminophenyl)phthalide in 58.8 g of an alkylbenzene. This solution was added to the aqueous mixture and the resulting mixture was emulsified using a variable speed one-half horsepower Eppenbach Homo-Mixer (Gifford-Wood Co., Hudson, N.Y.) at an applied voltage of 60 volts until droplets are smaller than five microns. While maintaining the rapid aggitation 22.5 g of 50 percent aqueous Resimene 714 (methylated methylol melamine resin produced by Monsanto Chemical Co.) was added over 3 to 5 minutes. After the microcapsules had formed the suspension was transferred to a round bottom glass flask equipped with a conventional blade type laboratory agitator and stirred approximately two hours at approximately 50° C. The mixture then was stirred overnight at ambient temperature. The mixture was adjusted to pH 7.0 with the addition of concentrated aqueous sodium hydroxide.

B. The microcapsule suspension prepared in part A above was coated on paper sheets to a thickness of approximately 0.0015 inch and the coated sheets of paper air dried. The paper thus coated with the microencapsulated colorless precursor was assembled as the top sheet in a manifold system by positioning the coated side in contact with the coated side of a commercially-available receiving sheet coated with a color developer of the electron-accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color-developing substance on the receiving sheet whereupon a color image immediately formed. On the acidic clay receiving sheet the image was a deep blue color. On the phenolic resin receiving sheet the image was a cyan color. Both developed images exhibited good tinctorial strength, excellent xerographic copiability characteristics and excellent light stability.

EXAMPLE 68

The utility of the compounds of Formulas I, II, and III, as color forming components in thermal marking systems is illustrated by the incorporation and testing of the compound of Example 1, 3-[1-(2-methoxyethyl)-2-methylindol-3-yl]-2-(2-methyl-4-diethylaminophenyl)phthalide in a thermal-responsive marking paper. The test paper was prepared by a procedure similar to that described in U.S. Pat. No. 3,539,375.

A. A mixture of 2.0 g of 3-[1-(2-methoxyethyl)-2-methylindol-3-yl]-3-(2-methyl-4-diethylaminophenyl)phthalide, 7.1 g of a ten percent aqueous solution of polyvinyl alcohol (approximately 99 percent hydrolized), 8.6 g of distilled water and 31.6 g of 1/16 inch diameter zirconium grinding beads was charged into a container which was placed in a mechanical shaker. Shaking was effected for one hour. The zirconium beads were than removed by straining the mixture through a No. 40 sieve.

B. Similarly, a mixture of 9.8 g of 4,4'-isprooylidine diphenol (Bisphenol A), 42.0 g of a ten percent aqueous polyvinyl alcohol solution (approximately 99 percent hydrolized), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.5 g of the slurry from part A and 22.5 g of the slurry from part B. The mixture was then uniformly coated on sheets of paper at a thickness of approximately 0.0015 inch and the coated sheets air dried. The coated paper placed on a smooth flat surface with a stylus heated to approximately 125° C. An intense cyan-colored image corresponding to the traced design promptly developed.

EXAMPLE 69

The use of the compounds of Formulas I, II, and III described in the foregoing examples, as color-forming components in transfer imaging systems is illustrated by testing the compound of Example 1, 3-[1-(2-methoxyethyl)-2-methylindol-3-yl]-3-(2-methyl-4-diethylaminophenyl)phthalide on a paper coated with color developer of the type used in transfer imaging systems as described in U.S. Pat. No. 4,399,209. A solution was prepared by dissolving 1.0 g of 3-[1-(2-methoxyethyl)-2-methylindol-3-yl]-2-(2-methyl-4-diethylaminophenyl)phthalide in 100.0 ml of toluene. A sample of the toluene solution was coated onto a commercially prepared developer sheet for use in a transfer imaging system containing the developer material. Immediately upon contact with the developer sheet the product in the toluene formed a cyan-colored image. The developed image posssessed excellent tinctorial strength, exhibited excellent stability to light and was readily copiable on xerographic copying machines.

Similarly, the solutions of the products of Example 3; 3-[1-(2-ethoxyethyl)-2-methylindol-3-yl]-3-(2-methyl-4-diethylaminophenyl)phthalide and Example 7, 3-[1-(2-phenoxyethyl)-2-methylindol-3-yl)-3-(2-methyl-4-diethylaminophenyl)phthalide were coated onto commercial developer coated paper sheets and all developed deep cyan-colored images which exhibited properties similar to those of product of Example 1.

What is claimed is:

1. A 3-(1-R-2-$R^1$-5/6-Y-indol-3-yl)-3-(2-$R^2$-4-N-$R^3$-N-$R^4$-aminophenyl)-X-phthalide having the formula

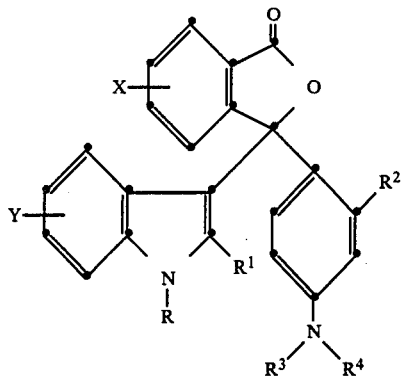

wherein:
R represents alkylene-O-$R^5$ in which alkylene represent —$C_2H_4$— or —$C_3H_7$— and $R^5$ represent non-tertiary $C_1$ to $C_6$ alkyl;
$R^1$ represents non-tertiary $C_1$ to $C_4$ alkyl or phenyl;
$R^2$ represents hydrogen, ahlogen, non-tertiary $C_1$ to $C_4$ alkyl, non-tertiary $C_1$ to $C_8$ alkoxy, dialkylamino in which alkyl is non-tertiary $C_1$ to $C_4$ alkyl, N-alkylamido in which alkyl is non-tertiary $C_1$ to $C_4$ alkyl, or trifluoromethyl
$R^3$ and $R^4$ independently represent non-tertiary $C_1$ to $C_8$ alkyl, alkylene-O-$R^5$, alkylene-O-alkylene-O-$R^5$ benzyl, or benzyl substituted in the phenyl ring by one or two non-tertiary $C_1$ to $C_4$ alkyl, non-tertiary $C_1$ to $C_4$ alkoxy, halo or nitro, or $R^3$ and $R^4$, taken together with the nirtogen represent piperidinyl, pyrrodidinyl or morpholinyl;
X represents

in which Z represent $OR^6$ wherein $R^6$ represents hydrogen, a non-teriary $C_1$ to $C_{16}$ alkyl, benzyl or benzyl substituted in the phenyl ring by one or two of non-teriraty $C_1$ to $C_4$ alkyl, non-tertiary $C_1$ to $C_4$ alkoxy, halo or nitro, or one to four halogen; and
Y represents hydrogen or one or two non-tertiary $C_1$ to $C_4$ alkyl, non-tertiary $C_1$ to $C_4$ alkoxy, halo or nitro.

* * * * *